(12) United States Patent
Gellman et al.

(10) Patent No.: US 6,958,384 B2
(45) Date of Patent: Oct. 25, 2005

(54) POLYPEPTIDES CONTAINING γ-AMINO ACIDS

(75) Inventors: Samuel H. Gellman, Madison, WI (US); Matthew G. Woll, Madison, WI (US); Jonathan R. Lai, Madison, WI (US); Justin Murray, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/389,500

(22) Filed: Mar. 14, 2003

(65) Prior Publication Data

US 2003/0211999 A1 Nov. 13, 2003

Related U.S. Application Data

(60) Provisional application No. 60/364,406, filed on Mar. 15, 2002.

(51) Int. Cl.[7] .............................................. C07K 2/00
(52) U.S. Cl. ..................................... 530/332; 530/300
(58) Field of Search ............................... 530/300, 332, 530/350

(56) References Cited

PUBLICATIONS

Abele, Guichard, & Seebach (1998) "(S)–β³–homolysine– and (S)–β³–homoserine–containing β–peptides: CD spectra in aqueous solution," *Helv. Chim. Acta* 81:2141.

Appella, Christianson, Karle, Powell, & Gellman (1996) "β–Peptide Foldamers: Robust Helix Formation in a New Family of β–Amino Acid Oligomers," *J. Am. Chem. Soc.* 118:13071.

Appella, Christianson, Klein, Powell, Huang, Barchi, & Gellman (1997) Residue–Based Control of Helix Shape in β–Peptide Oligomers *Nature* 387:381.

Appella, Christianson, Karle, Powell & Gellman (1999) "Synthesis and Characterization of trans–2–Aminocyclohexanecarboxylic Acid Oligomers: An Unnatural Secondary Structure, and Implications for β–Peptide Tertiary Structure," *J. Am. Chem. Soc.* 121:6206.

Appella, Christianson, Klein, Richards, Powell, & Gellman (1999) "Synthesis and Characterization of Helix–Forming β–Peptides: trans–2–aminocyclopentanecarboxylic acid oligomers," *J. Am. Chem. Soc.* 121:7574.

Barchi, Huang, Appella, Christianson, Durell, & Gellman (2000) "Solution Conformations of Helix–Forming β–Amino Acid Homooligomers," *J. Am. Chem. Soc.* 122:2711.

Blaskovich, Lin, Delarue, Sun, Park, Coppola, Hamilton, & Sebti (2000) "Desing of GFB–111, a platelet–derived growth factor binding molecule with antiangiogenic and anticancer activity against human tumors in mice," *Nature Biotechnol.* 18:1065.

(Continued)

*Primary Examiner*—Jeffrey Edwin Russel
(74) *Attorney, Agent, or Firm*—Joseph T. Leone, Esq.; DeWitt Ross & Stevens S.C.

(57) ABSTRACT

Disclosed are polypeptide compounds containing at least one residue comprising a cyclically-constrained γ-amino acid residue. The compounds have the formula

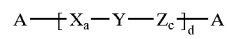

where A is a hydrogen, hydroxy, amino- or carboxy-protecting group, Y is a single bond or a prolyl-containing linking group, and X and Y are γ-amino acid residues, provided that one of X or Y is a conformationally-restrained γ-amino acid residue, and "a," "c," and "d" are positive integers. The compounds find use as non-enzymatically degradable probes to mimic protein behavior in solution.

26 Claims, 3 Drawing Sheets

OTHER PUBLICATIONS

Bolm, Schiffers, Dinter, & Gerlach (2000) "Practical and highly enantioselective ring opening of cyclic meso–anhydrides mediated by cinchona alkaloids," *J. Org. Chem.* 65:6984.

Bothner–By, Stephens, Lee, Warren, & Jeanloz R. W. (1984) *J. Am. Chem. Soc.* (1984) 106:811.

Braunschweiler & Ernst (1983) *J. Magn. Reson.* 53:521.

Cammers–Goodwin, Allen, Oslick, McClure, Lee, & Kemp (1996) "Mechanism of stabilization of helical conformations of polypeptides by water containing trifluoroethanol," *J. Am. Chem. Soc.* 118:3082.

Chin & Schepartz (2001) "Concerted evolution of structure and function in a miniature protein," *J. Am. Chem. Soc.* 123:2929.

Chung, Huck, Christianson, Stanger, Krauthauser, Powell & Gellman (2000) *J. Am. Chem. Soc.* 122:3995.

Cochran (2000) "Antagonists of protein–protein interactions," *Chem. Biol.* 7:R85.

Curran, Chandler, Kennedy, & Keaney (1996) "N–α–Benzoyl–cis–4–amino–L–proline: a γ–turn mimetic," *Tetrahedron Lett.* 37:1933.

Dado and Gellman (1994) *J. Am. Chem. Soc.* 116:1054–1062.

Fisk, Powell, & Gellman (2000) *J. Am. Chem. Soc.* 122:5443.

Degrado, Schneider, & Hamuro (1999) Journal of Peptide Research 54:206.

Gellman (1998) *Acc. Chem. Res.* 31:173.

Gellman (1998) "Minimal model systems for β–sheet secondary structure in proteins," *Curr. Opin. Chem. Biol.* 2:717.

Gómez–Vidal & Silverman (2001) "Short, highly efficient syntheses of protected 3–azido– and 4–azidoproline and their precursors," *Org. Lett.* 3:2481.

Goodman, Verdini, Toniolo, Phillips, & Bovey (1969) *Proc. Natl. Acad. Sci. USA* 64:444.

Gung, Zou, Stalcup, & Cottrell, (1999) "Characterization of a water–soluble, helical β–peptide," *J. Org. Chem.* 64:2176.

Hamuro et al. (1999) *J. Am. Chem. Soc.* 121:12200–12201.

Hanessian, Luo, Schaum, Michnick (1998) "Design of secondary structures in unnatural peptides: stable helical γ–tetra–, hexa–, and octapeptides and consequences of α–substitution," *J. Am. Chem. Soc.* 120:8569.

Hanessian, Luo, Schaum (1999) Tetrahedron Lett. 40:4925.

Hintermann, Gademann, Jaun, Seebach (1998) "γ–Peptides forming more stable secondary structures than α–peptides: synthesis and helical NMR–solution structure of the γ–hexapeptide analog of H–(Val–Ala–Leu)$_2$–OH," *Helv. Chim. Acta* 81:983.

Kobayashi, Kamiyama, & Ohno (1990) "Chiral synthon obtained with pig–liver esterase–introduction of chiral centers into cyclohexene skeleton," *Chem. Pharm. Bull.* 38:350–354.

Kobayashi, Kamiyama, & Ohno (1990) "The first enantioselective synthesis of fortamine, the 1,4–diaminocyclitol moiety of fortimicin–A, by chemicoenzymatic approach," *J. Org. Chem.* 55:1169.

Lacroix, Kortemme, Lopez Do La Paz, & Serrano (1999) *Curr. Opin. Struct. Biol.* 9:487.

Lee, Syud, Wang, Gellman (2001) "Diversity in Short β–Peptide 12–Helices: High Resolution Structural Analysis in Aqueous Solution of a Hexamer Containing Sulfonylated Pyrrolidine Residues," *J. Am. Chem. Soc.* 123:7721.

Luo & Baldwin (1997) "Mechanism of helix induction by trifluoroethanol: a framework for extrapolating the helix–forming properties of peptides from trifluoroethanol/water mixtures back to water," *Biochemistry* 36:8413.

Macura & Ernst (1980) *Mol. Phys.* 41:95.

Raghothama, Awasthi, Balaram, (1998) "β–Hairpin nucleation by Pro–Gly β–turns. Comparison of D–Pro–Gly and L–Pro–Gly sequences in an apolar octapeptide," *J. Chem. Soc., Perkin Trans.* 2:137.

Seebach et al. (1996) *Helv. Chim. Acta.* 79:913–941.

Seebach et al. (1996) *Helv. Chim. Acta.* 79:2043–2066.

Seebach & Matthews (1997), Chem. Commun. 2015–2022.

Seebach, Brenner, Rueping, Schweizer, Jaun (2001) "Preparation and determination of x–ray–crystal and NMR–solution structures of $\gamma^{2,3,4}$–peptides," *Chem. Commun.* 207.

Suhara et al. (1996) *Tetrahedron Lett.* 37(10):1575–1578.

Walgers, Lee, & Cammers–Goodwin, (1998) "An indirect chaotropic mechanism for the stabilization of helix conformation of peptides in aqueous trifluoroethanol and hexafluoro–2–propanol," *J. Am. Chem. Soc.* 120:5073.

Wang, Liu, Zhang, Shan, Han, Srinivasula, Croce, Alnemri, & Huang (2000) "Structure–based discovery of an organic compound that binds Bcl–2 protein and induces apoptosis of tumor cells," *Proc. Natl. Acad. Sci. USA* 97:7124.

Woll, Lai, Guzei, Taylor, Smith, Gellman, (2001) "Parallel Sheet Secondary Structure in γ–Peptides," *J. Am. Chem. Soc.*, vol. 123, pp. 11077–11078.

Zutshi, Brickner, & Chmielewski (1998) "Inhibiting the assembly of protein–protein interfaces," *Curr. Opin. Chem. Biol.* 2:62.

POLYPEPTIDES CONTAINING γ-AMINO ACIDS

Priority is hereby claimed to provisional application Ser. No. 60/364,406, filed Mar. 15, 2002, and incorporated herein by reference.

FEDERAL FUNDING STATEMENT

This invention was made with United States government support awarded by the following agencies: NSF 9820952. The United States has certain rights in this invention.

FIELD OF THE INVENTION

The invention is directed to polypeptides comprising cyclically-constrained γ-amino acids. These novel, unnatural peptidomimetics are resistant or wholly immune to peptidase and protease degradation and are conformationally restrained. Thus, they are useful as tools to model peptide and protein conformations in aqueous solutions. The compounds are also useful as non-enzymatically degradable probes to mimic protein behavior in solution.

DESCRIPTION OF THE RELATED ART

Chemists have long sought to extrapolate the power of biological catalysis and recognition to synthetic systems. These efforts have focused largely on low molecular weight catalysts and receptors. Most biological systems, however, rely almost exclusively on large polymers such as proteins and RNA to perform complex chemical functions. Predicting and modeling the solution-phase behavior of these large molecules has also been an on-going and sustained effort conducted by many groups.

Proteins and RNA are unique in their ability to adopt compact, well-ordered conformations. These two biopolymers are unique also because they can perform complex chemical operations (e.g., catalysis, highly selective recognition, etc.). Folding is linked to function in both proteins and RNA because the creation of an "active site" requires proper positioning of reactive groups. Consequently, there has been a long-felt need to identify synthetic polymer backbones which display discrete and predictable folding propensities (hereinafter referred to as "foldamers") to mimic natural biological systems. Such backbones will provide molecular "tools" to probe the functionality of large-molecule interactions (e.g. protein-protein and protein-RNA interactions). Insofar as these unnatural backbones are resistant to the action of proteases and peptidases, they are useful as probes having constrained conformational flexibility. Whereas a naturally occurring, α-amino acid probe will be readily degraded by any number of proteases and peptidases, foldamers are not.

Much work on β-amino acids and peptides synthesized therefrom has been performed by a group led by Dieter Seebach in Zurich, Switzerland. See, for example, Seebach et al. (1996)[a] and Seebach et al. (1996)[b]. In the first of these two papers Seebach et al. describe the synthesis and characterization of a β-hexapeptide, namely (H-β-HVal-β-HAla-β-HLeu)$_2$-OH. Interestingly, this paper specifically notes that prior art reports on the structure of β-peptides have been contradictory and "partially controversial." In the second paper, Seebach et al. explore the secondary structure of the above-noted β-hexapeptide and the effects of residue variation on the secondary structure.

Dado and Gellman (1994) describe intramolecular hydrogen bonding in derivatives of β-alanine and γ-amino butyric acid. This paper postulates that β-peptides will fold in manners similar to α-amino acid polymers if intramolecular hydrogen bonding between nearest neighbor amide groups on the polymer backbone is not favored.

Suhara et al. (1996) report a polysaccharide analog of a β-peptide in which D-glycocylamine derivatives are linked to each other via a C-1 β-carboxylate and a C-2 α-amino group. This class of compounds has been given the trivial name "carbopeptoids."

Hamuro et al. (1999) describe antibacterial compositions containing β-peptides having a repeating 3-peptide residue motif. The compounds described are: Fmoc-(β$^3$-HVal-β$^3$-HLys-β$^3$-HLeu)$_n$-OH (n=2–4); H-(β$^3$-HVal-β$^3$-HLys-β$^3$-HLeu)$_n$-OH (n=2–4); and H-(β$^3$-HLeu-β$^3$-HLys-β$^3$-HLeu)$_n$-OH (n=2–6). While these β-peptides are described as being antibacterial, they are also hemolytic at concentrations near the effective antibacterial concentrations, thus limiting their utility as medicaments.

As noted above, the interest in foldamers stems in part from their resistance to enzymatic degradation. They are also interesting molecules because of their conformational behavior. The elucidation of foldamers having discrete conformational propensities akin to those of natural proteins has led to numerous recent explorations of peptides constructed from β-, γ-, or δ-amino acids. For recent reviews, see, for example, Seebach & Matthews (1997), Gellman (1998)[a] and Degrado et al. (1999). γ-Peptides containing residues bearing γ-substitution or α,γ-disubstitution or α,β,γ-trisubstitution have been shown to adopt a helical conformation defined by a 14-member turn that is stabilized by C=O(i)→NH(i+3) hydrogen bonds. See Hintermann et al. (1998) and Hanessian et al. (1998). Hanessian et al. (1999) have reported reverse turn formation by a γ-peptide built from α,γ-disubstituted residues having a stereochemistry that is different from that leading to helical folding.

In the hairpin loop architecture, found in natural proteins, two strands of the amino acid backbone of the molecule are connected by a short loop. The hairpin loop is essential for creating small increments of β-sheet secondary structure in conventional peptides. See Gellman (1998)[b] and Lacroix et al. (1999). Formation of β-sheet secondary structure requires non-covalent attraction between the strand segments, as well as an appropriate conformational propensity in the loop segment. Subtle variations in the covalent structure of the strand segments can prevent sheet formation. See, for example, Fisk, Powell, & Gellman (2000). The loop segment, however, need not be constructed from the same components as the strand segments. Several investigators have shown that non-peptide loops can allow anti-parallel β-sheet interactions between appended α-amino acid strands. Parallel β-sheet hairpins require a non-peptide loop because the strands must be linked C-terminus to C-terminus (or N-terminus to N-terminus). Anti-parallel sheet secondary structure has been documented in β-peptides containing both non-β-peptide and β-peptide linkers. See, for example, Chung et al. (2000).

BRIEF DESCRIPTION OF THE DRAWING FIGURES

FIG. 5 is a series of superimposed circular dichroism (CD) spectra of the γ-amino acid and homo-oligomers of

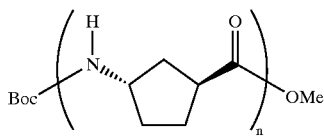

where n=1 to 6

DETAILED DESCRIPTION OF THE INVENTION

Figure 1:
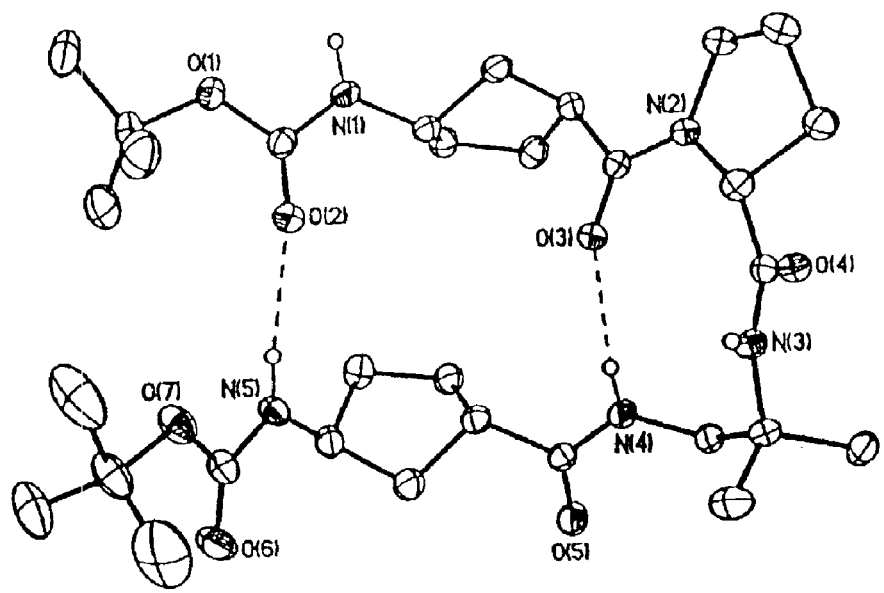
FIG. 1 is a model depicting the solid state crystal structure of compound 1. All hydrogen atoms, except those attached to nitrogen, have been omitted for clarity.

Abbreviations and Definitions:

The following abbreviations and definitions are used throughout the specification and claims. Terms not expressly defined herein are to be given their conventional and accepted definition within the field of synthetic organic chemistry.

The term "alkyl," by itself or as part of another substituent, means, unless otherwise stated, a fully saturated, straight, branched chain, or cyclic hydrocarbon radical, or combination thereof, and can include di- and multi-valent radicals, having the number of carbon atoms designated (e.g., $C_1$–$C_{10}$ means from one to ten carbon atoms, inclusive). Examples of alkyl groups include, without limitation, methyl, ethyl, n-propyl, isopropyl, n-butyl, t-butyl, isobutyl, sec-butyl, cyclohexyl, (cyclohexyl)ethyl, cyclopropylmethyl, and homologs, and isomers thereof, for example, n-pentyl, n-hexyl, n-heptyl, n-octyl, and the like. The term "alkyl," unless otherwise noted, also includes those derivatives of alkyl defined in more detail below as "heteroalkyl" and "cycloalkyl."

The term "alkenyl" means an alkyl group as defined above containing one or more double bonds. Examples of alkenyl groups include vinyl, 2-propenyl, crotyl, 2-isopentenyl, 2-(butadienyl), 2,4-pentadienyl, 3-(1,4-pentadienyl), etc., and higher homologs and isomers.

The term "alkynyl" means an alkyl or alkenyl group as defined above containing one or more triple bonds. Examples of alkynyl groups include ethynyl, 1- and 3-propynyl, 3-butynyl, and the like, including higher homologs and isomers.

The terms "alkylene," "alkenylene," and "alkynylene," alone or as part of another substituent means a divalent radical derived from an alkyl, alkenyl, or alkynyl group, respectively, as exemplified by —$CH_2CH_2CH_2CH_2$—.

Typically, alkyl, alkenyl, alkynyl, alkylene, alkenylene, and alkynylene groups will have from 1 to 24 carbon atoms. Those groups having 10 or fewer carbon atoms are preferred in the present invention. The term "lower" when applied to any of these groups, as in "lower alkyl" or "lower alkylene," designates a group having 10 or fewer carbon atoms.

"Substituted" refers to a chemical group as described herein that further includes one or more substituents, such as lower alkyl, aryl, acyl, halogen (e.g., alkylhalo such as $CF_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkyl, alkenyl, alkynyl, alkylene, alkenylene, and alkynylene moieties. Additionally, these groups may be pendent from, or integral to, the carbon chain itself.

The term "heteroalkyl," by itself or in combination with another term, means, unless otherwise stated, a stable, saturated or unsaturated, straight, branched chain, or cyclic hydrocarbon radical, or combinations thereof, consisting of the stated number of carbon atoms and from one to three heteroatoms selected from the group consisting of O, N, Si, and S, and wherein the nitrogen and sulfur atoms may optionally be oxidized and the nitrogen heteroatom(s) may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as in —$CH_2$—NH—O—$CH_3$ and —$CH_2$—O—Si($CH_2$)$_3$. Explicitly included within the term "heteroalkyl" are those radicals that could also be described as "heteroalkylene" (i.e., a divalent radical, see next paragraph), and "heterocycloalkyl" (i.e., containing a cyclic group). The term "heteroalkyl" also explicitly includes unsaturated groups (i.e., heteroalkenyls and heteroalkynyls).

The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini. Still further, for alkylene and heteroalkylene linking groups, no orientation of the linking group is implied.

The term "aryl" is used herein to refer to an aromatic substituent, which may be a single aromatic ring or multiple aromatic rings which are fused together, linked covalently, or linked to a common group such as a diazo, methylene or ethylene moiety. The common linking group may also be a carbonyl as in benzophenone. The aromatic ring(s) may include, for example phenyl, naphthyl, biphenyl, diphenylmethyl and benzophenone, among others. The term "aryl" encompasses "arylalkyl" and "substituted aryl." For phenyl groups, the aryl ring may be mono-, di-, tri-, tetra-, or penta-substituted. Larger rings may be unsubstituted or bear one or more substituents.

"Substituted aryl" refers to aryl as just described including one or more functional groups such as lower alkyl, acyl, halogen, alkylhalo (e.g., $CF_3$), hydroxy, amino, alkoxy, alkylamino, acylamino, acyloxy, phenoxy, mercapto, and both saturated and unsaturated cyclic hydrocarbons which are fused to the aromatic ring(s), linked covalently or linked to a common group such as a diazo, methylene, or ethylene moiety. The linking group may also be a carbonyl such as in cyclohexyl phenyl ketone. The term "substituted aryl" encompasses "substituted arylalkyl."

The term "acyl" is used to describe a ketone substituent, —C(O)R, where R is substituted or unsubstituted alkyl, alkenyl, alkynyl, or aryl as defined herein. The term "carbonyl" is used to describe an aldehyde substituent. The term "carboxy" refers to an ester substituent or carboxylic acid, i.e., —C(O)O— or —C(O)—OH.

The term "halogen" or "halo" is used herein to refer to fluorine, bromine, chlorine and iodine atoms.

The term "hydroxy" is used herein to refer to the group —OH.

The term "amino" is used to designate NRR', wherein R and R' are independently H, alkyl, alkenyl, alkynyl, aryl or substituted analogs thereof. "Amino" encompasses "alkylamino," denoting secondary and tertiary amines, and "acylamino" describing the group RC(O)NR'.

The term "alkoxy" is used herein to refer to the —OR group, where R is alkyl, alkenyl, or alkynyl, or a substituted analog thereof. Suitable alkoxy radicals include, for example, methoxy, ethoxy, t-butoxy, etc. The term "alkoxyalkyl" refers to ether substituents, monovalent or divalent, e.g. —CH$_2$—O—CH$_3$ and —CH$_2$—O—CH$_2$—.

"ACHC"=3-aminocyclohexanecarboxylic acid
"ACPC"=3-aminocyclopentanecarboxylic acid
"BOC"=t-butoxycarbonyl
"BOP"=bis(2-oxo-3-oxazolidinyl) phosphonic acid
"Cbz"=carbobenzyloxycarbonyl
"CD"=far UV circular dichroism spectroscopy
"COSY"=correlated spectroscopy
"DCC"=N,N'-dicyclohexylcarbodiimide
"DCM"=dichloromethane
"DEAD"=diethyl azodicarboxylate
"DIC"=diisopropylcarbodiimide
"DIEA"=diisopropylethyl amine
"DMAP"=4-dimethylaminopyridine
"DMF"=dimethylformamide
"EDCI"=1-{3-(dimethylamino)propyl}-3-ethylcarbodiimide
"EDT"=ethanedithiol
"Fmoc"=9-fluorenylmethoxy carbonyl
"Fmoc-OSu"=9-fluorenylmethyl succinimidyl carbonate
"HOBt"=1-hydroxybenzotriazole
"HBTU"=2-(benzotriazol-1-yl)-1,1,3,3-tetramethyluronium hexafluorophosphate
"NMP"=N-methyl pyrrolidinone
"NMR"=nuclear magnetic resonance spectroscopy
"NOESY"=nuclear Overhauser effect spectroscopy
"PMA"=phosphomolybdic acid stain
"PyBOP"=benzotriazol-1-yl-oxytripyrrolidinophosphonium hexafluorophosphate
"ROESY"=rotational nuclear Overhauser effect spectroscopy
"TFA"=trifluoroacetic acid
"THF"=tetrahydrofuran
"TLC"=thin-layer chromatography
"TOCSY"=total correlation spectroscopy Overview of Compounds:

In a first embodiment, the invention is directed to an unnatural polypeptide compound containing at least one residue comprising a cyclically-constrained γ-amino acid residue. Here, the invention is directed to unnatural polypeptide compounds selected from the group consisting of:

(i)

wherein:
each Y is independently variable and is selected from the group consisting of a single bond or

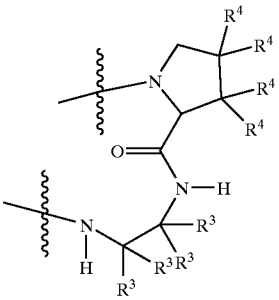

(ii)

where each $R^3$ is independently variable and is selected from the group consisting of hydrogen, linear or branched $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, and mono- or bicyclic heteroaryl-$C_1$–$C_6$-alkyl.

Each $R^4$ is selected from the same group of substituents as listed below for $R^1$.

Each X and each Z in formula (i) is independently variable and is selected from the group consisting of γ-amino acid residues, provided that at least one of X or Z is a cyclically-constrained γ-amino acid residue independently selected from the group consisting of:

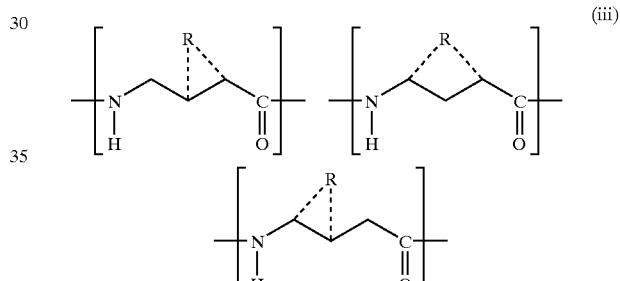

(iii)

wherein R, together with the carbons to which it is attached, and further together with the β-position carbon in the γ-amino acid backbone where appropriate, independently defines a substituted or unsubstituted $C_5$ to $C_{10}$ cycloalkyl, cycloalkenyl, or heterocycle moiety, the heterocycle moiety having 1, 2, or 3 heteroatoms selected from the group consisting of N, S, and O. Nitrogen and sulfur are the preferred heteroatoms, nitrogen being the most preferred.

Each of "a", "c", and "d" is an independently variable positive integer. It is preferred that a+c≧3, and still more preferred that a+c+d≧6, although this is not required of the invention.

The "A" moiety of formula (i) is selected from the group consisting of hydrogen, hydroxy, an amino-terminus protecting group, and a carboxy-terminus protecting group. Thus, for amino termini, the "A" moiety is a hydrogen or an amino-terminus protecting group; for carboxy termini, the "A" moiety is a hydroxy group or carboxy-terminus protecting group. Salts of these compounds, pharmaceutical salts or otherwise, are included within the scope of the invention.

It is preferred that R in formula (iii), together with the carbons to which it is attached (and the carbon at the position β to the carbonyl group where appropriate), defines a substituted or unsubstituted $C_5$ to $C_6$ cycloalkyl, cycloalkenyl, or heterocycle moiety having a single nitrogen heteroatom.

When R in formula (iii), together with the carbons to which it is attached (and together with the carbon at the position β to the carbonyl group where appropriate), defines a substituted cyclic moiety, the substituents on the cycloalkyl, cylcloalkenyl, or heterocycle moieties are independently selected from the group consisting of linear or branched $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, —$(CH_2)_{n+1}$—$OR^2$, —$(CH_2)_{n+1}$—$SR^2$, —$(CH_2)_{n+1}$—$S(=O)$—$CH_2$—$R^2$, —$(CH_2)_{n+1}$—$S(=O)_2$—$CH_2$—$R^2$, —$(CH_2)_{n+1}$—$NR^2R^2$, —$(CH_2)_{n+1}$—$NHC(=O)R^2$, —$(CH_2)_{n+1}$—$NHS(=O)_2$—$CH_2$—$R^2$, —$(CH_2)_{n+1}$—$O$—$(CH_2)_m$—$R^1$, —$(CH_2)_{n+1}$—$S$—$(CH_2)_m$—$R^1$, —$(CH_2)_{n+1}$—$S(=O)$—$(CH_2)_m$—$R^1$, —$(CH_2)_{n+1}$—$S(=O)_2$—$(CH_2)_m$—$R^1$, —$(CH_2)_{n+1}$—$NH$—$(CH_2)_m$—$R^1$, —$(CH_2)_{n+1}$—$N$—$\{(CH_2)_m$—$R^1\}_2$, —$(CH_2)_{n+1}$—$NHC(=O)$—$(CH_2)_{n+1}$—$R^1$, —$(CH_2)_{n+1}$—$NHS(=O)_2$—$(CH_2)_m$—$R^1$; —$(CH_2)_n$—$OR$, —$(CH_2)_n$—$SR^2$, —$(CH_2)_n$—$S(=O)$—$CH_2$—$R^2$, —$(CH_2)_n$—$S(=O)_2$—$CH_2$—$R^2$, —$(CH_2)_n$—$NR^2R^2$, —$(CH_2)_n$—$NHC(=O)R^2$, —$(CH_2)_n$—$NHS(=O)_2$—$CH_2$—$R^2$, —$(CH_2)_n$—$O$—$(CH_2)_m$—$R^1$, —$(CH_2)_n$—$S$—$(CH_2)_m$—$R^1$, —$(CH_2)_n$—$S(=O)$—$(CH_2)_m$—$R^1$, —$(CH_2)_n$—$S(=O)_2$—$(CH_2)_m$—$R^1$, —$(CH_2)_n$—$NH$—$(CH_2)_m$—$R^1$, —$(CH_2)_n$—$N$—$\{(CH_2)_m$—$R^1\}_2$—$(CH_2)_n$—$NHC(=O)$—$(CH_2)_m$—$R^1$, and —$(CH_2)_n$—$NHS(=O)_2$—$(CH_2)_m$—$R^1$; wherein $R^2$ is independently selected from the group consisting of hydrogen, $C_1$–$C_6$-alkyl, alkenyl, or alkynyl; mono- or bicyclic aryl, mono- or bicyclic heteraryl having up to 5 heteroatoms selected from N, O, and S; mono- or bicyclic aryl-$C_1$–$C_6$-alkyl, mono- or bicyclic heteroaryl-$C_1$–$C_6$-alkyl; and wherein $R^1$ is selected from the group consisting of hydroxy, $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxylate esters, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$–$C_6$-alkyl, aryl, heteroaryl; O-alkylurethane, O-arylurethane, and O-heteroarylurethane, wherein m is an integer of from 2–6 and n is an integer of from 0–6.

It is generally preferred that one of X or Z is a γ-amino acid residue wherein R in formula (iii), together with the carbons to which it is attached (and the carbon at the position β to the carbonyl group where appropriate), independently defines a substituted or unsubstituted cyclopentyl, substituted or unsubstituted cyclohexyl, unsubstituted or N-substituted piperidinyl, or unsubstituted or N-substituted pyrrolidinyl.

When R in formula (iii), together with the carbons to which it is attached and the carbon at the position β to the carbonyl group, defines an unsubstituted cyclic moiety, it is preferred that the moiety be selected from the group consisting of:

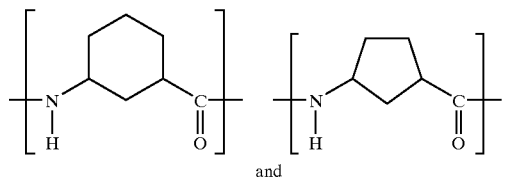

(iv)

and

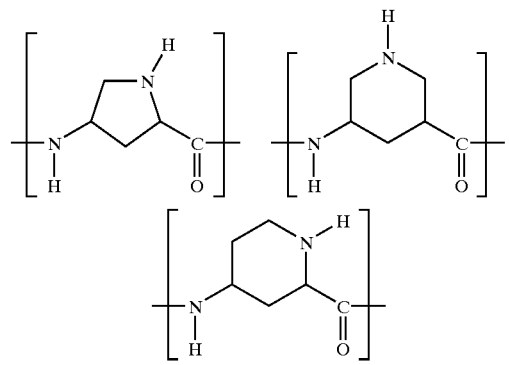

(v)

As used in the specification and the claims, the word "independently," when referring to the nature of a variable substituent, explicitly means that each appearance of the defined substituent within a molecule can be different. Thus, for example, in a molecule according to the present invention such as A-$X_3$-$Z_3$-B (where Y is a single bond, A is hydrogen, and B is hydroxy), each appearance of X and each appearance of Z can vary independently within the molecule. Thus, according to this explicit definition, the molecule A-$X_3$-$Z_3$-B explicitly encompasses the molecule A-X'-X"-X"'-Z'-Z"-Z"'-B, where X' may the same as or different from X", and X" may be the same as or different from X"'. Likewise, Z' may the same as or different from Z", and Z" may be the same as or different from Z"'.

As used herein, the terms "γ-amino acid" and "γ-amino acid residue" refer to any and all natural and unnatural γ-amino acids and their respective residues (i.e., the form of the amino acid when incorporated into a polypeptide molecule), without limitation. As used herein, the terms "amino-terminus protecting group" and "carboxy-terminus protecting group" refer to any chemical moiety capable of addition to and (optionally) removal from a reactive site (an amino group and a carboxy group, respectively, in this instance) to allow manipulation of a chemical entity at sites other than the reactive site. Protecting groups, and the manner in which they are introduced and removed are described, for example, in "Protective Groups in Organic Chemistry," Plenum Press, London, N.Y. 1973; and in "Methoden der organischen Chemie," Houben-Weyl, 4th edition, Vol. 15/1, Georg-Thieme-Verlag, Stuttgart 1974; and in Theodora W. Greene, "Protective Groups in Organic Synthesis," John Wiley & Sons, New York 1981. A characteristic of many protecting groups is that they can be removed readily, i.e., without the occurrence of undesired secondary reactions, for example by solvolysis, reduction, photolysis or alternatively under physiological conditions.

A host of protecting groups are known in the art. An illustrative, non-limiting list of protecting groups includes methyl, formyl, ethyl, acetyl, t-butyl, anisyl, benzyl, trifluoroacetyl, N-hydroxysuccinimide, t-butoxycarbonyl, benzoyl, 4-methylbenzyl, thioanizyl, thiocresyl, benzyloxymethyl, 4-nitrophenyl, benzyloxycarbonyl, 2-nitrobenzoyl, 2-nitrophenylsulphenyl, 4-toluenesulphonyl, pentafluorophenyl, diphenylmethyl, 2-chlorobenzyloxycarbonyl, 2,4,5-trichlorophenyl, 2-bromobenzyloxycarbonyl, 9-fluorenylmethyloxycarbonyl, triphenylmethyl, and 2,2,5,7,8-pentamethylchroman-6-sulphonyl. The terms "amino-terminus protecting group" and "carboxy-terminus protecting group" as used herein are explicitly synonymous with such terms as "N-terminal capping group" and "C-terminal capping group," respectively. A host of suitable protecting and capping groups, in addition to those described above, are known in the art. For discussions of various different types of amino- and carboxy-protecting groups, see, for example, U.S. Pat. No. 5,221,736 (issued Jun. 22, 1993); U.S. Pat. No. 5,256,549 (issued Oct. 26, 1993); U.S. Pat. No. 5,049,656 (issued Sep. 17, 1991); and U.S. Pat. No. 5,521,184 (issued May 28, 1996).

Regarding salts of the subject compounds, compounds having at least one basic group or at least one basic radical, for example a free amino group, a pyrazinyl radical, or a pyridyl radical, may form acid addition salts. Thus, the invention encompasses acid addition salts of the subject compounds with (for example) inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxybenzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid. When several basic groups are present mono- or poly-acid addition salts may be formed.

When the subject compounds have acidic groups, for example a free carboxy group, the invention encompasses metal and ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethylpiperidine or N,N'-dimethyl-piperazine.

Compounds of formula (i) having both acidic and basic groups can form internal salts. The salts may be pharmaceutically-acceptable salts or pharmaceutically-unacceptable salts.

Gamma Amino Acids and Polypeptides Formed Therefrom:

Molecular modeling studies performed by the inventors suggested that polypeptides containing γ-amino acid residues similar to trans-3-aminocyclopentanecarboxylic acid (trans-3-ACPC) residues would have a high propensity for γ-peptide parallel sheet secondary structure. Molecules exhibiting this type of secondary structure would be in stark contrast to the helical propensity previously documented for acyclic γ-amino acid residues.

Thus, molecules 1 and 2 were prepared. In each of these compounds, two (1S,3S)-trans-3-ACPC residues are linked via a D-prolyl-(1,1-dimethyl)-1,2-diaminoethyl unit:

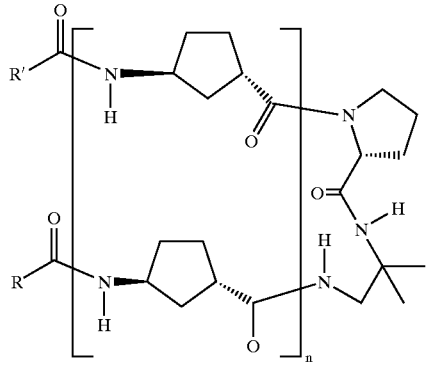

1: n=1, R=R'=OC(CH$_3$)$_3$
2: n=1, R=R'=CH$_2$Ph
3: n=2, R=CH$_2$Ph, R'=C(CH$_3$)$_3$

The diamine linker portion of compounds 1, 2, and 3 has previously been shown to allow parallel β-sheet formation between attached α-amino acid residue strand segments. See Fisk, Powell, & Gellman (2000).

Crystal structures of 1 and 2 show that both molecules adopt the desired hairpin conformation in the solid state. See FIGS. 1 and 2, which are solid-state crystal structures of compounds 1 and 2, respectively. These results, particularly the similarity between two independent structures, show that the non-γ-peptide linker allows a parallel sheet hydrogen bonding pattern between attached γ-peptide strands.

Molecule 2 was examined by two-dimensional NMR methods in CD$_2$Cl$_2$ (3.6 and 5.7 mM, 25° C.) to evaluate the propensity for parallel γ-peptide sheet formation under dynamic conditions. Under these conditions, molecule 2 exhibits little or no aggregation in solution. (The amide proton shifts of 2 displayed minimal variation over the concentration range of from about 0.3 mM to about 10 mM in CD$_2$Cl$_2$, indicating that there is little or no self-association of 2 under these conditions.) Previous work with small oligoamides, including hairpin molecules that contain α- and/or β-amino acid residues has shown that intramolecular hydrogen bonding provides a modest drive for folding in nonpolar solvents, but that sheet-type hydrogen bonding will not occur unless both the strand and the turn segments have suitable conformational propensities.

Figure 2:
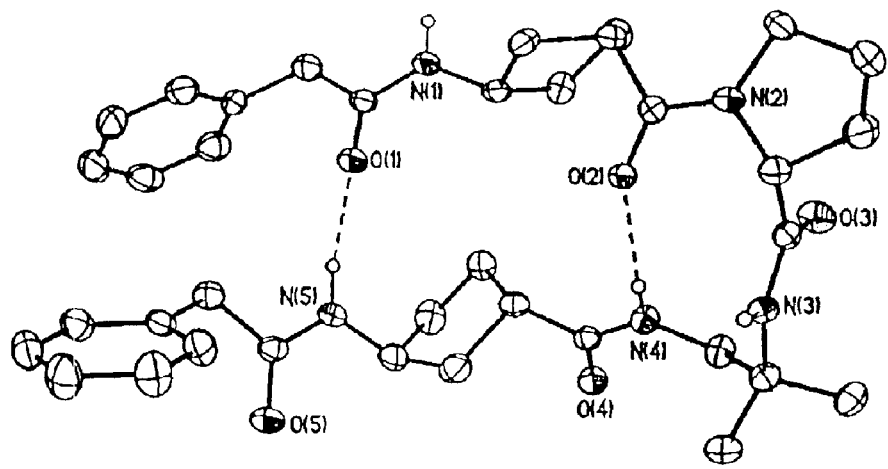
FIG. 2 is a model depicting the solid state crystal structure of compound 2. All hydrogen atoms, except those attached to nitrogen, have been omitted for clarity.

A combination of COSY (correlated spectroscopy), TOCSY (total correlation spectroscopy), and ROESY (rotational nuclear Overhauser effect spectroscopy) spectra provided sufficient data to allow nearly all of the proton resonances from 2 to be unambiguously assigned. This, in turn, enabled the use of the amide proton chemical shift data to gain preliminary insight on folding. In nonpolar solvents C=O to H—N hydrogen bond formation causes an increase (up to 2–3 ppm) in the chemical shift of an amide proton (δNH). Equilibria between hydrogen bonded and non-hydrogen bonded states are usually rapid on the NMR time scale, and observed δNH values are therefore weighted averages of the contributing hydrogen bonded and non-hydrogen bonded states. For compound 2 in CD$_2$Cl$_2$, the pattern of δNH values observed indicates that a significant population of the molecules adopt the conformation shown in FIG. 2; i.e., in solution, a significant proportion of compound 2 molecules adopt the same conformation as observed in the solid state. δNH-1 (5.52 ppm) and δNH (5.63 ppm) are consistent with little or no hydrogen bonding at these amide protons, while δNH-4 (7.04 ppm) and δNH-5 (7.24 ppm) indicate substantial hydrogen bond donation by these groups (using atom numbering as shown in FIG. 2).

More detailed structural insight was obtained from ROESY data for 2. Most informative among the short-range NOEs was one between the $C_\delta H$ of proline and the $C_\alpha H$ of the trans-3-ACPC residue attached to proline. This NOE showed that the tertiary amide linkage has the Z configuration in solution, as observed in both crystal structures shown in FIGS. 1 and 2. In addition, six NOEs between the two γ-amino acid residues (or immediately adjacent atoms) could be assigned unambiguously. See FIG. 3 for a graphic representation of these NOEs in compound 2. Five of these NOEs are consistent with the conformation observed for 2 in the solid state or modest distortions from this conformation: $C_\gamma H \rightarrow C_\alpha H$ (strong; 2.29 Å), $C_\gamma H \rightarrow$ linker NH (weak; 3.64 Å), $C_\gamma H \rightarrow C_\epsilon H$ (medium; 2.41 Å), $C_\gamma H \rightarrow NH$ (weak; 3.72 Å), and phenacyl $CH_2 \rightarrow NH$ (weak; 3.95 Å). (The distances given after NOE intensities were measured in the crystal structure of compound 2.)

Figure 3:
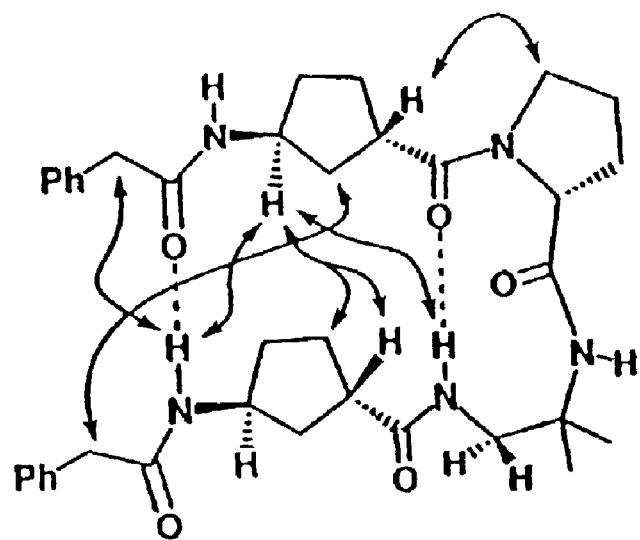
FIG. 3 is a graphic summary of selected NOEs for compound 2 (3.6 mM in CD$_2$Cl$_2$, 25° C.).

The sixth nonadjacent NOE shown in FIG. 3, $C_\beta H \rightarrow$ phenacyl $CH_2$ (weak), suggests that an alternative mode of interstrand interaction occurs to at least a small extent for 2 in $CD_2Cl_2$. This is because the shortest distance between protons on these two methylene groups is 5.91 Å in the crystal structure of 2.

Figure 4:
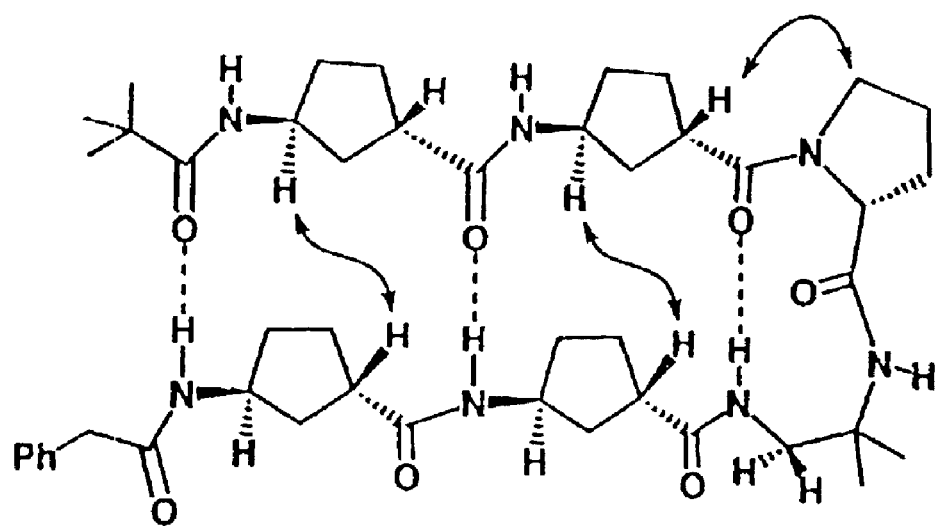
FIG. 4 is a graphic summary of selected NOEs for compound 3 (2 mM in pyridine-d5, 25° C.).

Molecule 3, which has two-residue γ-peptide strands on either side of the loop, was then synthesized and examined to determine whether parallel sheet secondary structure could propagate outward from the loop structure. Two-dimensional NMR analysis was carried out in pyridine-$d_5$ (2 mM, 25° C.) because compound 3 is nearly insoluble in $CD_2Cl_2$. Several key NOEs were unambiguously identified. See FIG. 4. The tertiary amide involving the proline nitrogen was shown to have the Z configuration by observation of a strong NOE between proline $C_\delta H$ and $C_\alpha H$ of the adjacent trans-3-ACPC residue. Strong $C_\gamma H \rightarrow C_\alpha H$ NOEs were observed between the inner pair of trans-3-ACPC residues and between the outer pair of trans-3-ACPC residues. These two NOEs indicate that in solutions of compound 3 there is a significant population of a hairpin conformation in which the parallel γ-peptide sheet involves all four trans-3-ACPC residues.

Thus, the present inventors have shown that the γ-peptides 1, 2, and 3 adopt sheet secondary structure in solution.

The utility of these compounds for probing protein interactions is great because, as noted above, the γ-peptides adopt structures analogous to those seen in natural proteins and peptides. Thus, the subject compounds mimic natural protein conformations in solution, but are resistant or immune to proteolytic degradation by proteases and peptidases. The cyclically-constrained γ-amino acid residues incorporated into homogeneous γ-peptide backbones are useful probes in the study of chemical and enzymatic interactions involving natural proteins. Also, the compounds disclosed herein add greatly to the γ-peptide field, in terms of both the number of alternative secondary structures that can be accessed and the intrinsic stability of those secondary structures. The subject compounds are useful probes because the cyclically-constrained residues create secondary structures with high conformational stability at short oligomer lengths that are also resistant to enzymatic degradation. The invention thus enhances the control over γ-peptide folding preferences, thereby providing a larger "toolbox" of probes to be used in investigating the function of naturally-occurring proteins.

Thus, the subject compounds are useful to implement a method of probing, disrupting, or mimicking binding interactions between two protein molecules or fragments thereof. The method comprises introducing to an in vivo, in vitro, or ex vivo reaction between two proteins, an unnatural polypeptide compound as described herein. Any effect of the added compound on thermodynamic or kinetic parameters of the binding interaction between the two protein molecules or fragments thereof is then measured. Because the subject compounds are conformationally similar to conventional α-polypeptides, but not subject to enzymatic degradation, the results provide valuable information regarding the interactions between large protein molecules.

Compounds 24a, an analog of 3, as well as higher analogs 24b and 24c are also easily prepared using the methods described herein. NMR analysis of these molecules in methanol, and other organic solvents, will show that the trans-4-aminopyrrolidinyl (trans-4-AP) residue supports γ-peptide hairpin formation in the same fashion as in compounds 1–3.

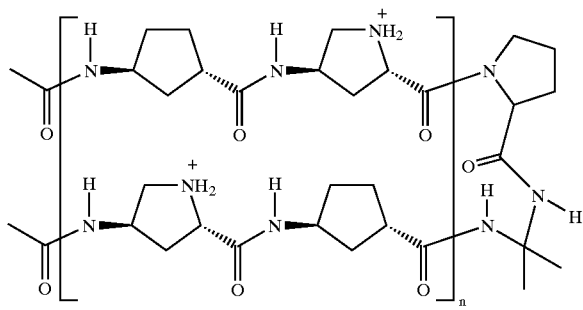

24a, n = 1
24b, n = 2
24c, n = 3

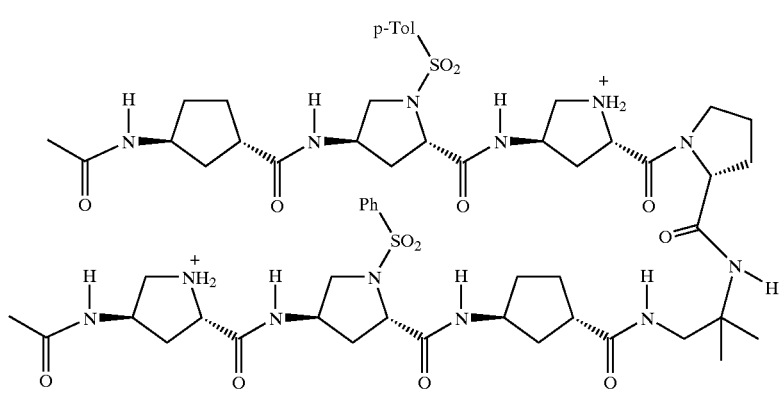

25

Because oligomers containing trans-4-AP display parallel sheet secondary structure in aqueous solution, diverse side-chains can be introduced into the rigidifying ring via sulfonylation of ring nitrogen atoms (e.g., as shown in compound 25). It has recently been shown that the ring nitrogen sulfonylation of pyrrolidine-based residues allows side-chain introduction in the β-peptide 12-helix, and this approach should function with equal success in the subject γ-peptides. See Lee et al. (2001). The design of 25 places hydrophobic side-chains across from one another, at the second residue of each strand. The crystallographic data for compounds 1 and 2 suggest that the parallel sheet conformation will be stabilized in water by clustering of the hydrophobic sulfonyl substituents.

Antiparallel γ-peptide secondary structure can be created by changing the linker used to connect strand segments. Initial studies will involve minimal hairpin molecules 26a–b, which have trans-3-ACHC residues in the strands.

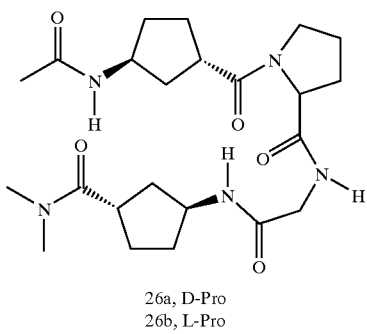

26a, D-Pro
26b, L-Pro

The prolyl-glycyl linker promotes strand interactions between α-amino acid residues. Gellman (1998)[b] and Rag-othama et al. (1998). Molecular modeling indicates that this linker is suitable for γ-residues as well.

Molecular modeling also indicates that a heterochiral dimer of cis-3-ACPC will form the γ-peptide analog of the familiar β-turn seen in α-peptides. This hypothesis can be tested by examining tetra-γ-peptides like compound 27.

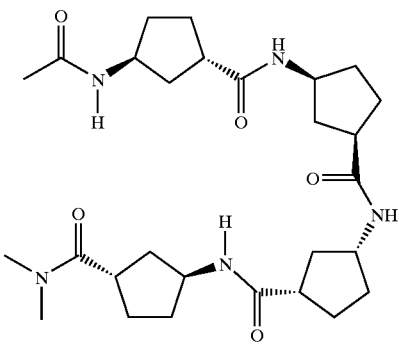

27

Functionally diverse antiparallel γ-peptide sheets that fold in water can thus be created by preparing analogs that contain amino-proline residues.

The only known type of γ-peptide helix was made exclusively with acyclic γ-amino acid residues; see Hintermann, Gademann, Jaun, Seebach (1998). Molecular modeling, however, indicates that two different cyclohexyl-rigidified residues, 28 and 29, will stabilize the γ-peptide 14-helix.

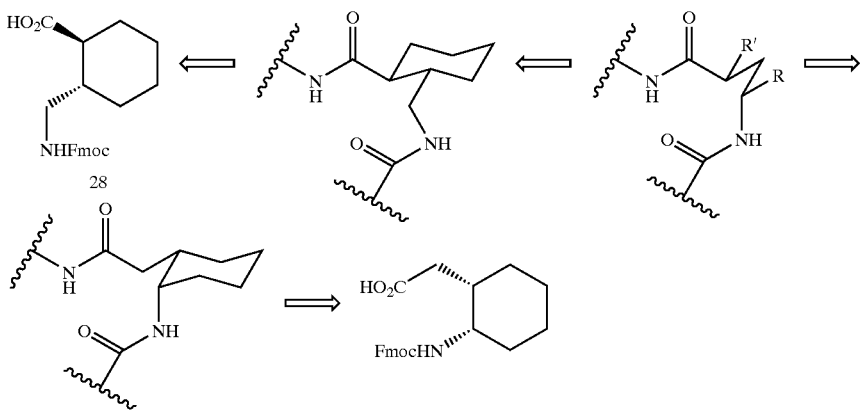

28

29

Both of these residues are available in enantiomerically pure form via straightforward extensions from or variations upon the synthetic routes currently in use, see Appella et al. (1999)[a], to provide the β-amino acid trans-2-aminocyclohexanecarboxylic acid (trans-2-ACHC). For example, an N-protected form of cis-2-ACHC subjected to an Arndt-Eisterdt homologation reaction, Goodman et al. (1969), would then provide the N-protected version of 29. Preparation of the Boc-protected analog of 28 would start with the reported enzymatic desymmetrization of cis-4,5-cyclohexenedicarboxylic acid dimethyl ester. See Scheme 1 and Kobayashi, Kamiyama, & Ohno (1990)[a] and (1990)[b]:

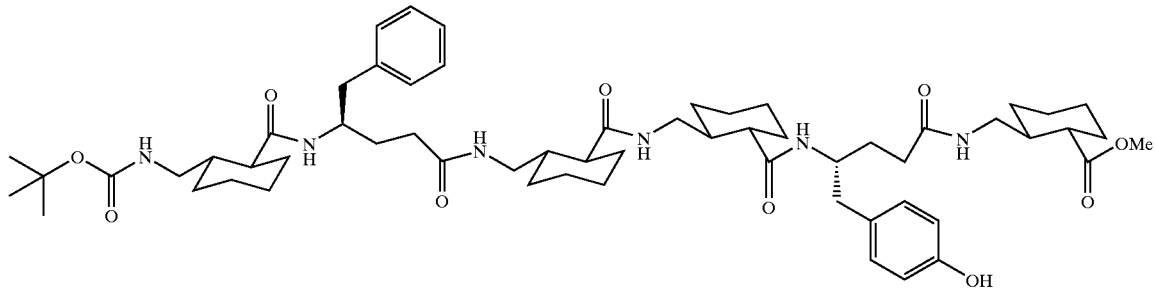

31

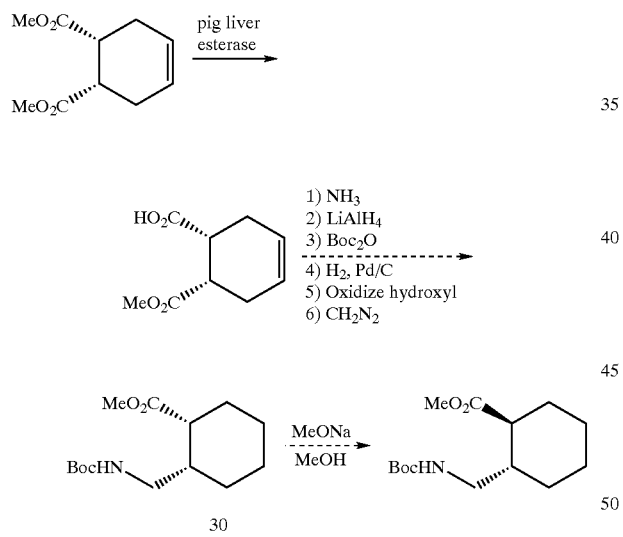

The half ester can be converted to either monoamide, and straightforward reactions will generate the protected cis-γ-amino acid 30. Kobayashi, Kamiyama, & Ohno (1990)[a] and (1990)[b] suggest that base-catalyzed epimerization will lead efficiently to the desired trans isomer, a protected form of 28.

Homo-oligomers of 28 and of 29, up to octamer length, are easily prepared using the linking chemistry described below. NMR analysis of these homooligomers, and co-oligomers of 28 and 29, in organic solvents, will reveal their conformational stability. Proton resonance overlap, however, may be too great to allow complete high-resolution structural analysis. If NMR analysis of these γ-peptides is fruitless, preparing γ-peptides containing a few scattered acyclic residues (e.g., hexamer 31) should enhance proton resonance dispersion.

The strategy of mixing cyclic and acyclic residues should also allow the fabrication of water-soluble γ-peptides that benefit from residue pre-organization. Various synthetic routes can then be used to make analogs that bear attachment sites for side-chains. For example, the route to trans-2-ACHC described above is applicable to commerically-available piperidine β-keto ester 32, which provides cis-amino ester 33 and ultimately protected γ-amino acid 34, an analog of 29 (Scheme 2):

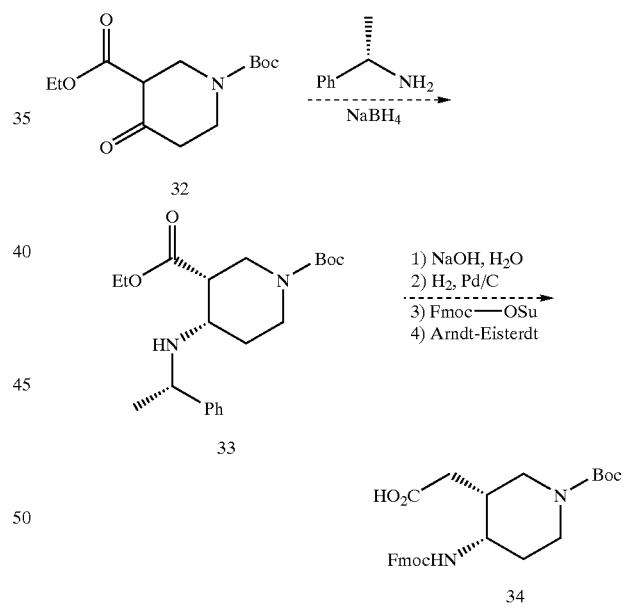

Equally useful for purposes of the present invention are cyclic γ-amino acids that are not expected to promote 14-helix formation based on the conformational analysis above, e.g., γ-amino acids 35–40:

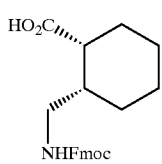

35

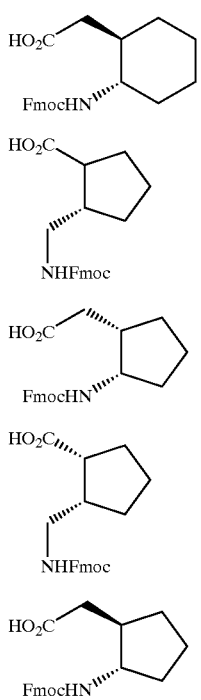

These studies provide unprecedented γ-peptide secondary structures (presumably helical). γ-Amino acids 35 and 36 are diastereomers of 28 and 29 that will disfavor the g$^+$,g$^+$ torsion sequence along the (O=)CC$_\alpha$—C$_\beta$C$_\gamma$ and C$_\alpha$C$_\beta$—C$_\gamma$N backbone bonds, while γ-amino acids 35–40 contain cyclopentane rings. See Scheme 8 for a detailed synthesis of compound 40; see Scheme 9 for a detailed synthesis of the Boc-derivative of compound 36. The switch from trans-cyclohexyl to trans-cyclopentyl constraint among β-amino acids causes a profound change in β-peptide secondary structure preference (14- to 12-helix), presumably because the cyclopentyl constraint does not promote 60° angles about the backbone C$_\alpha$—C$_\beta$ bond. See Appella et al. (1996), (1997), (1999)[a&b], and Barchi et al. (2000). (See Scheme 10 for a detailed synthesis of the trans isomer of compound 34.) By extrapolation, residues derived from 37–40 are expected to disfavor the γ-peptide 14-helix. There is, however, a strong likelihood that these residues will give rise to other discrete secondary structure preference(s) because of the very limited residue conformational freedom.

Synthesis of the necessary γ-peptide building blocks is accomplished as follows. For example, 30 in Scheme 2 is a precursor to 35. Asymmetric opening of the anhydride of cis-1,2-cyclopentanedicarboxylic acid, Bolm, Schiffers, Dinter, & Gerlach (2000), will lead to 38 and 39. Arndt-Eisterdt homologation of Fmoc-protected trans-2-ACPC will generate Fmoc-protected 40. Pyrrolidine derivatives of 37–40 are available via analogous routes. See the various Schemes given in the Examples section.

Chemistry:

General. Melting points are uncorrected. CH$_2$Cl$_2$ was freshly distilled from CaH$_2$ under N$_2$. DMF was distilled under reduced pressure from ninhydrin and stored over 4 Å molecular sieves. Triethylamine was distilled from CaH$_2$ before use. Other solvents and reagents were used as obtained from commercial suppliers. For BOC removal, 4 M HCl in dioxane from was used. Column chromatography was carried out by using low air pressure (typically 6 psi) with 230–400 mesh silica gel 60. Routine $^1$H-NMR spectra were obtained on a Bruker AC-300 and are referenced to residual protonated NMR solvent. Routine $^{13}$C-NMR spectra were obtained on a Bruker AC-300 and are referenced to the NMR solvent. High resolution electron impact mass spectroscopy was performed on a Kratos MS-80RFA spectrometer with DS55/DS90.

Infrared Spectroscopy. Spectra were obtained on a Nicolet Model 740 FT-IR spectrometer. IR samples were prepared under anhydrous conditions; CH$_2$Cl$_2$ was freshly distilled from CaH$_2$, compounds and glassware were dried under vacuum for 1–2 days, and solutions were prepared under a nitrogen atmosphere. The pure solvent spectrum for a particular solution was subtracted from the sample spectrum prior to analysis. Peaks in the amide NH stretch region were baseline corrected, and analyzed without further manipulation.

NMR Spectroscopy:

Aggregation Studies. One-dimensional spectra for aggregation studies were obtained on a Bruker AC-300 spectrometer. Samples for aggregation studies were prepared by serial dilution from the most concentrated sample (50 mM or 27 mM). Dry compounds were dissolved in CD$_2$Cl$_2$ previously dried over 3 Å molecular sieves, and samples were prepared with dry glassware under a nitrogen atmosphere.

Conformational Analysis. NMR samples for conformational analysis were prepared by dissolving the dry compound in dry deuterated solvent under a nitrogen atmosphere. CD$_2$Cl$_2$ samples were then degassed by the freeze-pump-thaw method, and the NMR tubes were sealed under vacuum. Methanol samples were sealed with a close fitting cap and parafilm. COSY spectra were obtained on a Bruker AC-300 spectrometer. TOCSY, Braunschweiler et al. (1983); NOESY, Macura & Ernst (1980); and ROESY, Bothner-By et al. (1984) spectra were acquired on a Varian Unity-500 spectrometer using standard Varian pulse sequences and hypercomplex phase cycling (States-Haberkorn method), and the data were processed with Varian "VNMR" version 5.1 software. Proton signals were assigned via COSY and TOCSY spectra, and NOESY and ROESY spectra provided the data used in the conformational analyses. TOCSY spectra were recorded with 2048 points in t$_1$, 320 or 350 points in t$_2$, and 8 or 40 scans per t$_2$ increment. NOESY and ROESY spectra were recorded with a similar number of t$_1$ and t$_2$ points, and 32 and 40 scans per t$_2$ increment, depending on the sample concentration. The width of the spectral window examined was between 2000 and 4000 Hz. Sample concentrations for two-dimensional spectra were 2 mM in CD$_2$Cl$_2$ or 8 mM in CD$_3$OD or CD$_3$OH, or 2 mM in pyridine-d$_5$.

Far UV Circular Dichroism (CD). Data were obtained on a Jasco J-715 instrument at 20° C. In all CD plots contained herein, the mean residue ellipticity is presented on the vertical axis. Presenting the mean residue ellipticity is a standard practice in peptide chemistry wherein the intensity of each CD spectrum is normalized for the number of amide chromophores in the peptide backbone. Consequently, when the intensities of the maximum and minimum peaks characteristic of secondary structure formation increase with increasing chain length, this change represents an increase in the population of the secondary structure, rather than simply an increase in the number of chromophores present in each molecule.

Solid-Phase and Solution-Phase Polypeptide Synthesis:

Construction of polypeptides using any type of γ-amino acid residue can be accomplished using conventional and widely recognized solid-phase or solution-phase synthesis.

Very briefly, in solid-phase synthesis, the desired C-terminal amino acid residue is linked to a polystyrene support as a benzyl ester. The amino group of each subsequent amino acid to be added to the N-terminus of the growing peptide chain is protected with Boc, Fmoc, or another suitable protecting group. Likewise, the carboxylic acid group of each subsequent amino acid to be added to the chain is activated with DCC, EDCI, PyBop, or another standard coupling reagent, and reacted so that the N-terminus of the growing chain always bears a removable protecting group. The process is repeated (with much rinsing of the beads between each step) until the desired polypeptide is completed. In the classic route, the N-terminus of the growing chain is protected with a Boc group, which is removed using trifluoracetic acid, leaving behind a protonated amino group. Triethylamine is used to remove the proton from the N-terminus of the chain, leaving a free amino group, which is then reacted with the activated carboxylic acid group from a new protected amino acid. When the desired chain length is reached, a strong acid, such as hydrogen bromide in trifluoracetic acid, is used to both cleave the C-terminus from the polystyrene support and to remove the N-terminus protecting group.

A representative solid-phase synthesis that can be used herein is shown in Scheme 3 (see also the Examples):

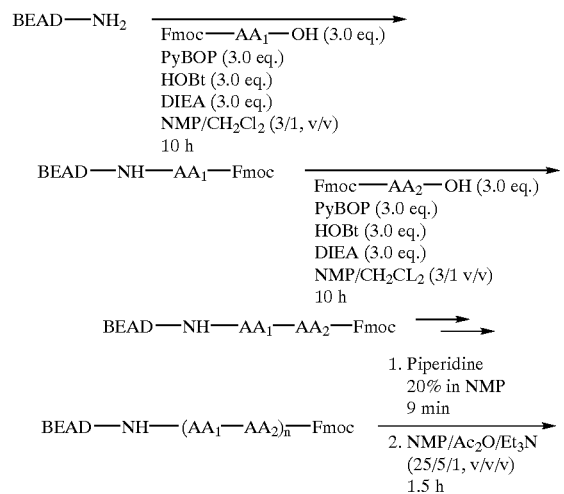

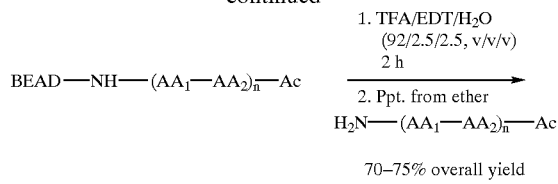

To begin each coupling, the Fmoc group on the resin bound amino acid/peptide is removed with 20% piperidine in N,N-dimethyl formamide (DMF). It is then rinsed and a protected amino acid is added which has been activated at its alpha carboxyl group. The activation is achieved by creating the N-hydroxybenzotriazole (HOBt) ester in situ. The activated A.A. and the resin bound A.A. are allowed to react in the presence of base to form a new peptide bond. This process is repeated until the desired peptide is assembled at the resin.

Once the peptide is complete, it is ready to be cleaved from the resin. This is accomplished using a mixture of trifluoroacetic acid (TFA) and any number of scavengers. Scavengers serve to neutralize cations which are formed during the removal of the side chain protecting groups. The cleavage solution is generally at least 82% TFA, and the rest a mixture of phenol, thioanisol, water, ethanedithiol (EDT), and triisopropylsilane (TIS). The peptide on the resin is allowed to react with the cleavage mixture for several hours, which then affords the peptide in solution. It can then be precipitated and washed in tert-butyl methyl ether, and analyzed or purified as desired.

Solid-phase peptide synthesis is, of course, widely employed and well known. There are several known variations on the above general approach. Consequently, solid-phase synthesis of peptides will not be described in any further detail. See, for example, "Peptide Synthesis, Structures, and Applications" © 1995 by Academic Press. Chapter 3 of this book addresses solid-phase peptide synthesis, and is incorporated herein by reference. Many of the subject γ-peptides can be made using the solid phase approaches described in this reference.

Solution phase synthesis, noted above, can also be used with equal success. For example, solution-phase synthesis of a γ-peptide chain can be accomplished as illustrated in the following coupling reaction:

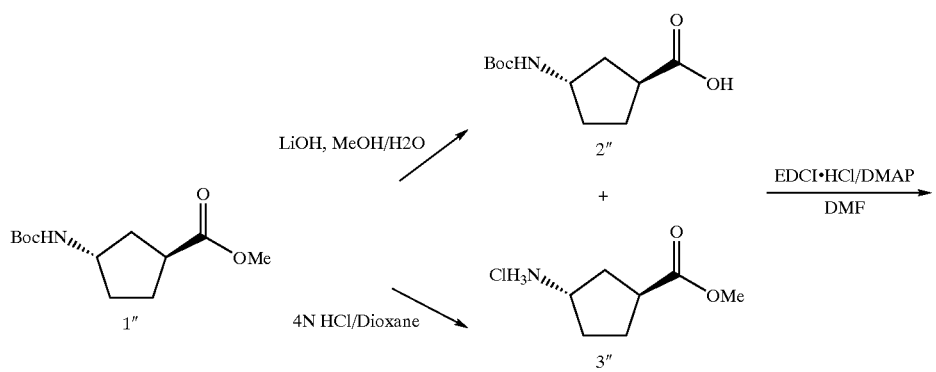

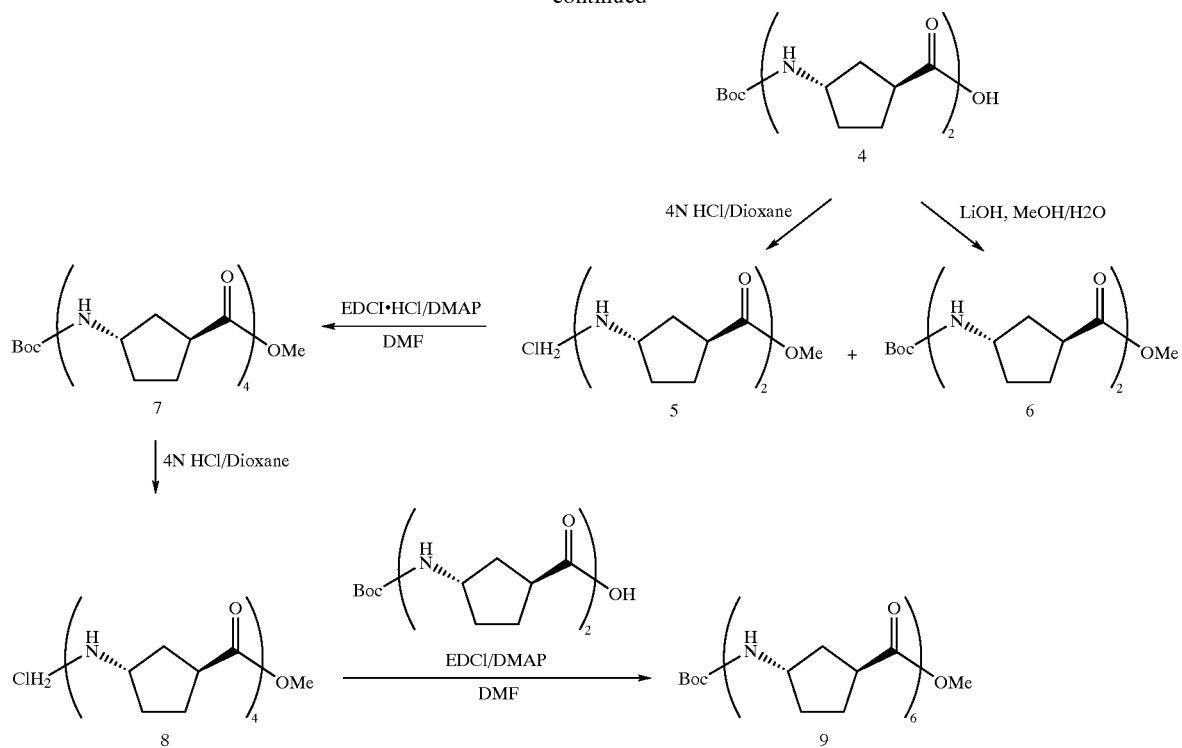

Compound 6: In 10 ml 5:1 MeOH:H$_2$O 4 (1.8 mmol) was dissolved. LiOH.H$_2$O (2.71 mmol) was added as a concentrated aqueous solution dropwise, maintaining the pH below 11. Solution stirred at RT 5 h. Neutralized with 0.5 M NaHSO$_4$ and evaporated MeOH. Acidified aqueous layer to pH 2. Extracted with EtOAc 2×. Dried organics with MgSO$_4$. 1.61 mmol of product was recovered, a white crystalline product. 93%.

Compound 7: To 0.56 mmol 4 was added 2 mL 4N HCl; in dioxane. After stirring at RT for one hour solvents were removed under a stream of nitrogen. Remaining residue was dissolved in DMF (3 mL). To the solution was added 6 (0.56 mmol), followed by DMAP (0.75 mmol), and EDCI (1.25 mmol). Solution stirred at RT 12 h. After about 1 h. a white precipate could be seen forming. 1 M HCl (2 mL) was added and the precipitate was filtered off and washed with water. Residue was then chromatographed with 20:1 CH$_2$Cl$_2$:MeOH. The product, a white powdery solid, was recovered in 88% yield. NMR was taken in 1:1 CDCl$_3$:CD$_3$OD due to poor solubility in other solvents.

All other compounds in Scheme 4 were synthesized in similar fashion. The hexamer 9 could not be chromatographed due to solubility issues, but was isolated pure by precipitation.

Figure 5:
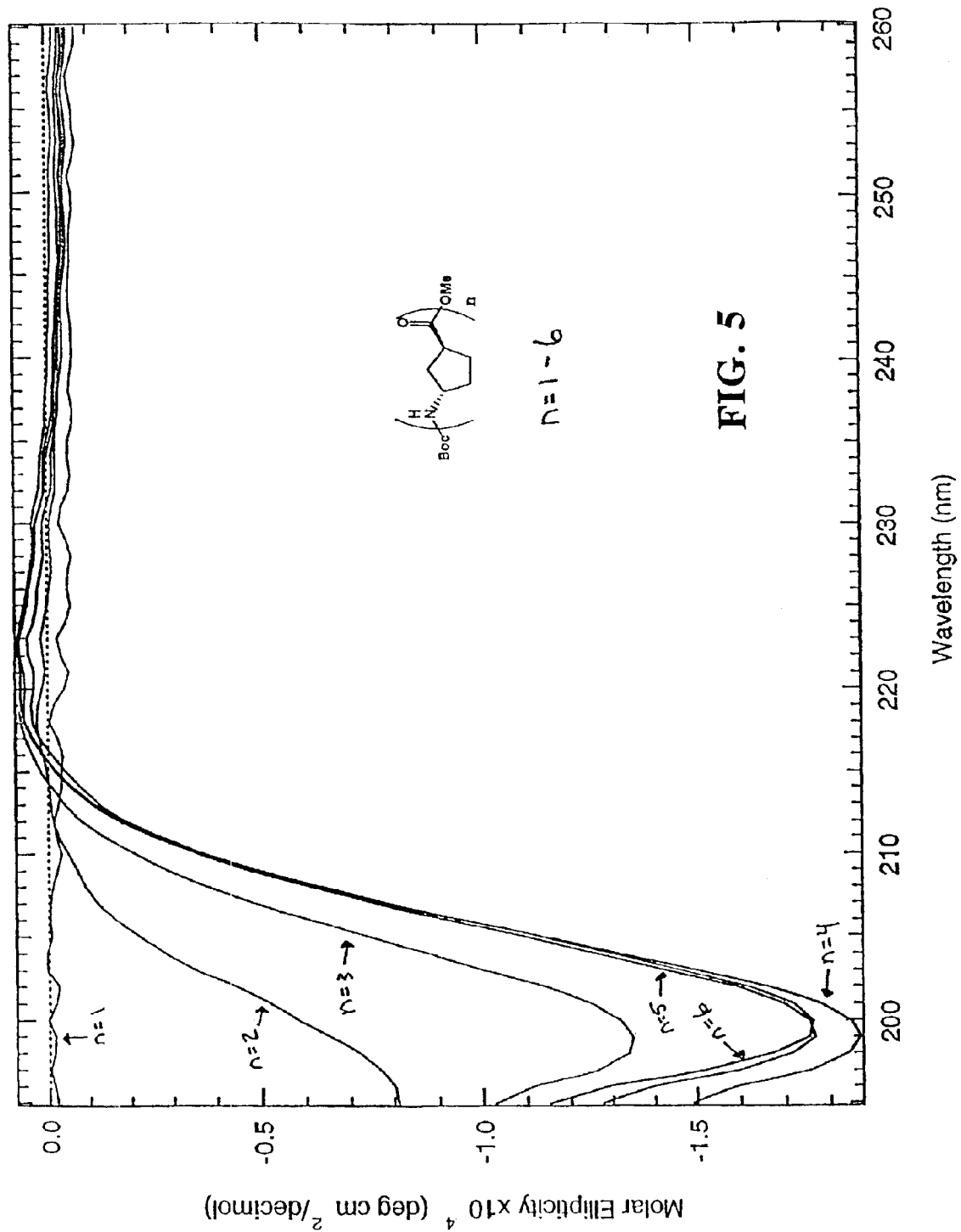

FIG. 5 is a series of superimposed CD spectra of the series leading from the monomer to the hexamer in the above coupling scheme. The spectra show the development of a characteristic minimum at about 190 nm, indicating the development of secondary conformation.

Adding Substituents to the Cyclic Moiety:

As noted above, the γ-peptides of the present invention can be substituted with any number of substituents, including hydroxy, linear or branched C$_1$–C$_6$-alkyl, alkenyl, alkynyl; hydroxy-C$_1$–C$_6$-alkyl, amino-C$_1$–C$_6$-alkyl, C$_1$–C$_6$-alkyloxy, C$_1$–C$_6$-alkyloxy-C$_1$–C$_6$-alkyl, amino, mono- or di-C$_1$–C$_6$-alkylamino, carboxamido, carboxamido-C$_1$–C$_6$-alkyl, sulfonamido, sulfonamido-C$_1$–C$_6$-alkyl, urea, cyano, fluoro, thio, C$_1$–C$_6$-alkylthio, mono- or bicyclic aryl, mono- or bicyclic heteraryl having up to 5 heteroatoms selected from N, O, and S; mono- or bicyclic aryl-C$_1$–C$_6$-alkyl, heteroaryl-C$_1$–C$_6$-alkyl, and combinations thereof. Effecting such substitutions is well within the set of skills possessed by a synthetic peptide chemist.

For example, appending a sulfonamido moiety to the cylic backbone substituent can be accomplished in conventional fashion using Reaction 10. This reaction depicts the addition of a sulfonamido moiety to the cyclic back bone of a β-peptide. The same approach, however, will function using the analogous γ-peptide starting materials.

Compound 63: Compound 61 (90 mg) was dissolved in 4 N HCl in dioxane (2.0 ml). The reaction mixture was stirred for 1.5 hours. The dioxane was then removed in vacuo. The residue was dissolved in pyridine (2.0 ml), then cooled to 0° C. in an ice-bath.

Methanesulfonylchloride (71 μl) was added dropwise. After the addition, the reaction mixture was stirred at room temperature for 12 hours. The pyridine was then removed in vacuo. The residue was taken up in ethyl acetate (50 ml). The mixture was washed with dilute brine (2×10 ml), dried over MgSO$_4$, and concentrated to give the clean product as a colorless oil (70 mg) in 82% yield.

Compound 64: Compound 62 (30 mg) was dissolved in 4 N HCl in dioxane (2.0 ml). The reaction mixture was stirred for 1.5 hours. The dioxane was then removed in vacuo. The residue was dissolved in pyridine (1.0 ml), then cooled to 0° C. in an ice-bath. Toluenesulfonylchloride (63 mg) was added in portions. After the addition, the reaction mixture was stirred at room temperature for 12 tours. The pyridine was then removed in vacuo. The residue was taken up in methylene chloride/diethyl ether (1/1, v/v, 100 ml). The mixture was washed with dilute brine (3×20 ml), dried over MgSO$_4$, and concentrated to give a liquid residue. The crude product was purified by column chromatography with ethyl acetate/hexane (4/6, v/v) as eluent to give the clean product as a colorless oil (25 g) in 74% yield.

Analogous reactions will append a carboxyamido group.

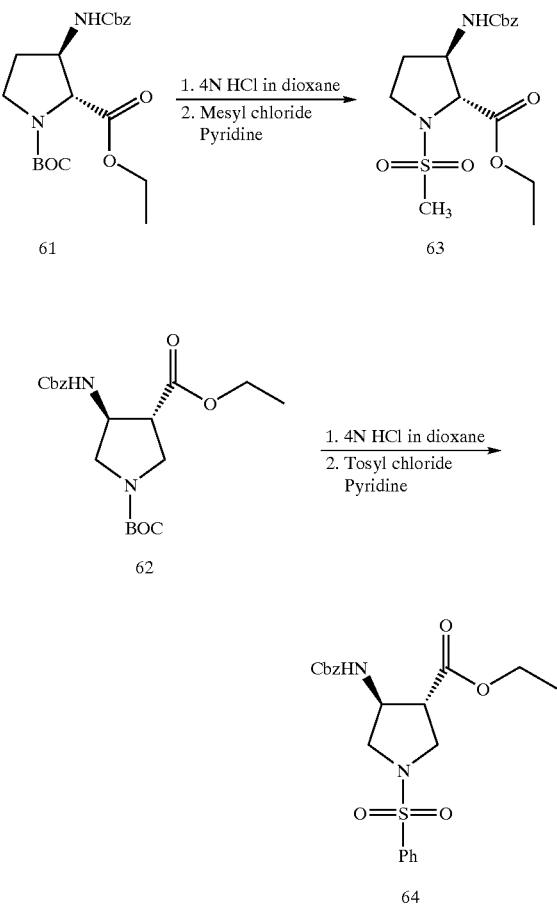

Scheme 5

61

62

63

64

EXAMPLES

The following Examples are included solely to provide a more complete and consistent understanding of the invention disclosed and claimed herein. The Examples do not limit the scope of the invention claimed herein in any fashion.

See Schemes 6–10 for the structures of the various intermediate and final products.

General Procedures for All Examples: THF was distilled from sodium/benzophenone ketyl under $N_2$. Triethylamine was distilled from calcium hydride. All commercially available reagents and solvents were purchased from Aldrich (Milwaukee, Wis.) and used without further purification, except for 4 N HCl in dioxane, which was purchased from Pierce Chemical (Rockford, Ill.), and Fmoc-OSu, which was purchased from Advanced ChemTech (Louisville, Ky.). Analytical thin-layer chromatography (TLC) was carried out on Whatman TLC plates pre-coated with silica gel 60 (250 μm layer thickness). Visualization was accomplished using a UV lamp and phosphomolybdic acid (PMA) stain (10% phosphomolybdic acid in ethanol), or $KMnO_4$ stain. Column chromatography was performed on EM Science silica gel 60 (230–400 mesh). Solvent mixtures used for TLC and column chromatography are reported in v/v ratios.

{(1R,2S)-2-tert-Butoxycarbonylamino-cyclopentyl}-acetic acid (Boc-γ-ACPC-OH): (1S,2S)-2-Amino-cyclopentanecarboxylic acid ($NH_2$-ACPC-OH, JKMI91, 5.18 g, 40.1 mmol) (See LePlae, Umezawa, Lee & Gellman (2001) *J. Org. Chem.* 66:5629–5632) was dissolved in methanol (409 mL). Triethylamine (11.16 mL, 80.2 mmol) was added via syringe followed by di-tert-butyl-dicarbonate (8.74 g, 40.1 mmol). The reaction mixture was stirred at room temperature for 2 h. The solvent was removed by rotary evaporation. The residue was diluted with ethyl acetate (250 mL), washed with 0.5 M $NaHSO_4$ (1×100), and saturated aqueous NaCl solution (1×100). The organic layer was dried over $MgSO_4$, filtered, and concentrated to give a white solid. The crude product was purified by column chromatography (7:3:0.3) hexane:ethyl acetate:acetic acid). Acetic acid was removed on the high-vacuum rotary evaporator. Benzene (2×100 mL) was added and removed on the rotary evaporator. The residue was dried under high vacuum overnight to give a white solid (Boc-ACPC-OH, JKMI103, 7.65 g, 83%). $^1$H NMR (250 MHz, $CDCl_3$): δ=11.22 (br. s, 1H), 4.93 (br. s, 1H), 4.02 (br. s, 1H), 2.69 (br. s, 1H), 2.14–1.89 (m, 3H), 1.68 (quin., J=6.7 Hz, 2H), 1.51–1.35 (m, 10H) ppm.

(1R,2S)-2-tert-Butoxycarbonylamino-cyclopentanecarboxylic acid (Boc-ACPC-OH): JKMI103 (6.94 g, 30.3 mmol) was placed in an oven-dried flask with a clear-seal joint containing an oven-dried stir bar and dissolved in dry THF (61 mL) under a $N_2$ atmosphere. The solution was cooled to −14° C. with an ice/brine bath. N-methylmorpholine (3.50 mL, 31.8 mmol) and isobutylchloroformate (4.13 mL, 31.8 mmol) were added via syringe. The mixture was stirred for 1 h and allowed to warm to 0° C. A white precipitate formed during this time. The flask was then fitted with an oven-dried "Diazald"-brand distillation apparatus (for generating diazomethane; see, for example, Hudlicky (1980) *J. Org. Chem.* 45:5377), and the joint was sealed with parafilm. A solution of KOH (12 g, 214 mmol) in $H_2O$ (20 mL) and 2-methoxyethanol (16 mL) was placed in the well of the apparatus with a stir bar and heated to 75° C. A saturated solution of "Diazald"-brand reagent (N-methyl-N-nitroso-p-toluene-sulfonamide (19.5 g, 91 mmol) in diethyl ether (100 mL) was decanted into a dropping funnel attached to the apparatus. The vacuum adapter was fitted with a septum, and the system was placed under $N_2$. The cold finger was cooled to −78° C. with a dry ice/isopropanol mixture. The "Diazald" solution was then dropped into the KOH solution over a period of 30 min. The yellow diazomethane distilled over and condensed on the cold finger, and then dropped into the reaction mixture.

Once distillation of the diazomethane was complete, and the reaction mixture had a persistent yellow color, the "Diazald" apparatus was removed. The flask was stoppered, placed under $N_2$, and stirred for 4 h, being allowed to warm from 0° C. to room temperature. Acetic acid (1 mL) was then added to neutralize any excess diazomethane. The reaction mixture was diluted with diethyl ether (200 mL), washed with saturated aqueous $NaHCO_3$ (2×100 mL), aqueous HCl (1 N, 100 mL), and saturated aqueous NaCl solution (100 mL). The organic layer was dried over $MgSO_4$, filtered, and concentrated. The crude product was purified by column chromatography (8:2 hexane:ethyl acetate) to give a pale yellow solid (Boc-ACPC-$CHN_2$, JKMI125, 4.75 g, 62%). $^1$H NMR (250 MHz, $CDCl_3$): δ=5.58 (br. s, 1H), 4.70 (br. s, 1H), 3.99 (quin., J=6.3 Hz, 1H), 2.66 (br. s, 1H), 2.03–1.55 (m, 5H), 1.49–1.29 (m, 10H) ppm.

This solid (Boc-ACPC-CHN$_2$, JKMI125, 2.71 g, 10.68 mmol) was dissolved in water/dioxane (1/5, 480 mL), and the flask was covered in aluminum foil to exclude light. Silver benzoate (0.245 g, 10 mol %) was added as a catalyst, and the mixture was sonicated at room temperature under N$_2$ for 1 h. At 0° C., the solution was acidified to pH 2 with aqueous 0.5 M NaHSO$_4$. The solution was extracted with diethyl ether (4×150 mL). The organic layer was dried over MgSO$_4$, filtered, and concentrated to give a white solid. The crude product was purified by column chromatography (6:4:0.3 hexane:ethyl acetate:acetic acid). Acetic acid was removed on the high-vacuum rotary evaporator. Benzene (2×200 mL) was added and removed on the rotary evaporator. The residue was dried under high vacuum overnight to give a yellowish white solid (Boc-γ-ACPC-OH, JKMI127, 2.36 g, 91%). This compound exists as slowly interconverting rotamers. $^1$H NMR (300 MHz, CDCl$_3$): δ=11.63 (br. s, 1H), 6.53 (br. s, 1H), 5.04 (d, J=7.4 Hz, 1H), 3.59–3.46 (m, 1H), 2.65–2.55 (m, 1H), 2.28–2.23 (br. s, 1H), 2.07–1.93 (M, 3H), 1.66–1.24 (m, 12H) ppm. $^{13}$C NMR (62.9 MHz, CDCl$_3$): δ=178.04 (C), 157.84, 156.14 (C), 80.82, 80.75 (C), 58.20, 56.91 (CH), 42.84 (CH), 38.00 (CH$_2$), 32.38 (CH$_2$), 30.03 (CH$_2$), 28.45 (3CH$_3$), 21.51 (CH$_2$) ppm. MS-ESI: m/z=242.2 {M−H}$^-$, 485.3 {2M−H}$^-$.

Boc-(γ-ACPC)$_2$-OBn: This solid (Boc-γ-ACPC-OH, JKMI127, 1.00 g, 4.12 mmol) and CsCO$_3$ (1.34 g, 4.12 mmol) were dissolved in THF (41 mL). Benzyl bromide (0.53 mL, 4.44 mmol) was added, and the mixture was stirred at room temperature under N$_2$ covered in aluminum foil for 24 h. The mixture was diluted with ethyl acetate (200 mL) and washed with saturated aqueous NaHCO$_3$ (1×100 mL) and saturated aqueous NaCl (1×100 mL) solutions. The organic layer was dried over MgSO$_4$, filtered, and concentrated to give a white solid. The crude product was purified by column chromatography (8:2 hexane:ethyl acetate) and dried overnight under high vacuum to give white solid (Boc-γ-ACPC-OBn, JKMI129, 0.58 g, 42%). $^1$H NMR (300 MHz, CDCl$_3$): δ=7.40–7.30 (m, 5H), 5.12 (s, 2H), 4.59 (br. s, 1H), 3.57 (br. t, J=8.2 Hz, 1H), 2.65 (dd, J=15.8, 4.9 Hz, 1H), 2.32 (dd, J=15.6, 8.8 Hz, 1H), 2.11–1.88 (m, 3H), 1.70–1.59 (m, 2H), 1.43–1.21 (m, 11H) ppm.

The combined aqueous layers were acidified with acetic acid and extracted with ethyl acetate (3×75 mL) to isolate unreacted starting material (Boc-γ-ACPC-OH).

This white solid (Boc-γ-ACPC-OBn, JKMI129, 0.839 g, 2.52 mmol) was dissolved in 4 N HCl in dioxane (10 mL) and stirred under N$_2$ for three hours at room temperature. The solvent was blown off overnight under a stream of N$_2$. The residue was placed under high vacuum for one hour and then carried on without further purification (NH$_2$-γ-ACPC-OBn•HCl, JKMI133).

Boc-γ-ACPC-OH (JKMI127, 0.612 g, 2.52 mmol), NH$_2$-γ-ACPC-OBn•HCl (JKMI133, 0.679 g, 2.52 mmol), and 4-dimethylaminopyridine (1.076 g, 8.817 mmol) were dissolved in DMF (15 mL, anhydrous). The solution turned a pale orange color. To the solution was added 1-(3-dimethylaminopropyl)-3-ethylcarbodiimide hydrochloride (0.726 g, 3.78 mmol), and the reaction mixture was stirred under N$_2$ at room temperature overnight. The mixture was diluted with 100 mL ethyl acetate and washed with 0.5 M aqueous NaHSO$_4$ (1×75 mL), saturated aqueous NaHCO$_3$ (1×75 mL), and saturated aqueous NaCl (1×75 mL) solutions. The organic layer was dried over MgSO$_4$, filtered, and concentrated. The crude product was purified by column chromatography (1:1 hexane:ethyl acetate) to give a white solid (Boc-(γ-ACPC)$_2$-OBn, JKMI135, 1.004 g, 87%). $^1$H NMR (300 MHz, CDCl$_3$): δ=7.38–7.28 (m, 5H), 6.77 (d, J=7.0 Hz, 1H), 5.10 (s, 2H), 4.82 (d, J=7.8 Hz, 1H), 3.87 (quin., J=8.1 Hz, 1H), 3.56 (br. quin., J=7.8 Hz, 1H), 2.64 (dd, J=15.8, 4.9 Hz, 1H), 2.40–2.29 (m, 2H), 2.19–1.83 (m, 7H), 1.72–1.47 (m, 4H), 1.43–1.21 (m, 13H) ppm. MS-ESI: m/z=481.3 {M+Na}$^+$, 939.5 {2M+Na}$^+$.

Boc-(γ-ACPC)$_4$-OBn: Boc-(γ-ACPC)$_2$-OBn (JKMI135, 0.375 g, 0.819 mmol) was dissolved in methanol (8.2 mL), and the flask was flushed with N$_2$. To the flask was added Pd/C 10% (0.056 g), and the flask was attached to a Parr apparatus and shaken overnight at an H$_2$ pressure of 44 psi. The reaction mixture was filtered through a syringe filter and concentrated via rotary evaporation to give a white solid (Boc-(γ-ACPC)$_2$-OH, JKMI139, 0.289 g, 96%). The crude product was carried on without further purification.

Boc-(γ-ACPC)$_2$-OBn (JKMI135, 0.375 g, 0.819 mmol) was dissolved in 4N HCl in dioxane and stirred under N$_2$ at room temperature for 2 h. The solvent was blown off overnight under a stream of N$_2$. The residue was placed under high vacuum for 1 h. The residue (NH$_2$-(γ-ACPC)$_2$-OBn•HCl, JKMI141) was carried on without further purification.

Scheme 6

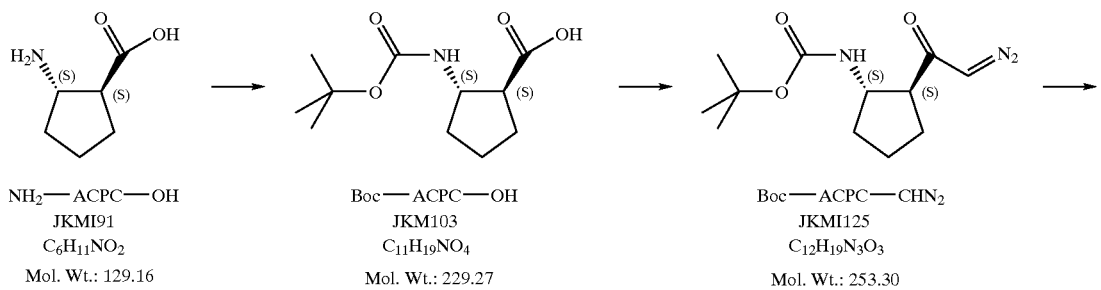

-continued

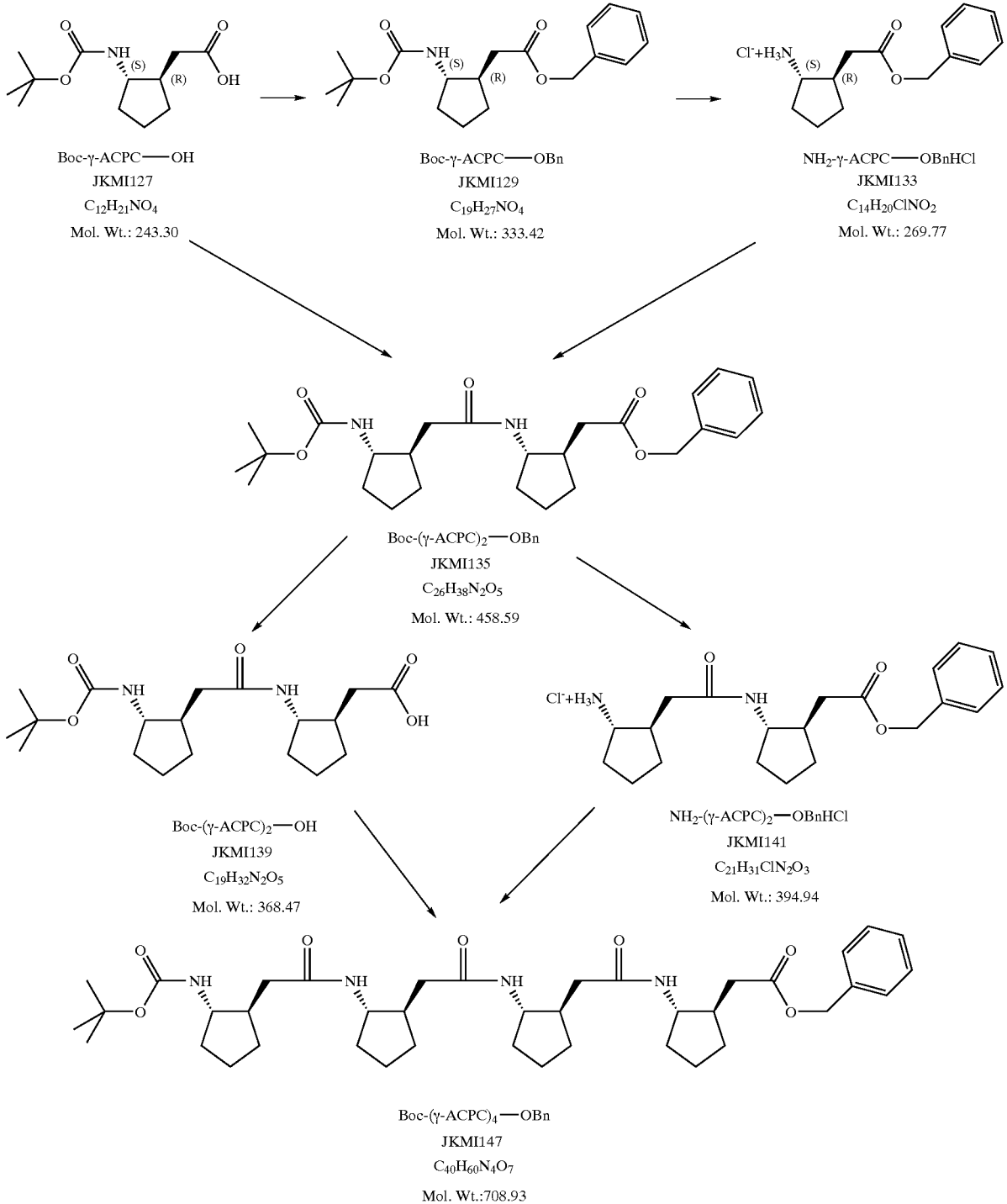

Boc-(γ-ACPC)₂-OH (JKMI139, 0.289 g, 0.786 mmol), NH₂-γ-ACPC-γ-ACPC-OBn•HCl (JKMI141), and 4-dimethylaminopyridine (0.350 g, 2.87 mmol) were dissolved in DMF (8.2 mL, anhydrous). To the solution was added 1-(3-dimethylaminopropyl)-3-ethylcarbodiimide hydrochloride (0.236 g, 1.23 mmol), and the reaction mixture was stirred under N₂ at room temperature overnight. A precipitate formed, and the solution turned pale orange during this time. Water (25 mL) was added to the reaction mixture to completely precipitate the product, which was then isolated by suction filtration. The solid was dissolved in CH₂Cl₂ (100 mL). The aqueous layer was extracted with CH₂Cl₂ (3×25 mL). The combined organic extracts were washed with 0.5 M aqueous NaHSO₄ (1×25 mL), saturated aqueous NaHCO₃ (1×25 mL), and saturated aqueous NaCl (1×25 mL) solutions. The organic layer was dried over MgSO₄, filtered, and concentrated. The organic layers were pooled, washed with saturated aqueous NaCl, dried over MgSO₄, and concentrated to give a white solid. The crude product was purified by column chromatography (CH₂Cl₂/

10% MeOH in CH$_2$Cl$_2$, loaded by adsorption to silica gel) to give a white solid (Boc-(γ-ACPC)$_4$-OBn, JKMI147, 0.306 g, 53%). $^1$H NMR (300 MHz, 10:1 CDCl$_3$:CD$_3$OD): δ=7.58 (br. s, 2H), 7.41–7.29 (m, 5H), 7.23 (br. s, 2H), 5.11 (s, 2H), 3.87–3.74 (m, 3H), 3.54–3.42 (m, 2H), 2.63 (dd, J=15.5, 4.3 Hz, 1H), 2.37–1.84 (m, 22H), 1.74–1.52 (m, 7H), 1.43–1.15 (m, 14H) ppm. MS-ESI: m/z=731.5 {M+Na}$^+$.

Boc-(γ-ACPC)$_6$-OBn: Boc-(γ-ACPC)$_4$-OBn (JKMI147, 0.150 g, 0.212 mmol) was dissolved in 4N HCl in dioxane (10 mL) and stirred under N$_2$ at room temperature for 2 h. The material fully dissolved, then a white precipitate formed. The solvent was blown off overnight under a stream of N$_2$. The residue was placed under high vacuum for 1 h. The residue (NH$_2$-(γ-ACPC)$_4$-OBn•HCl, JKMI151) was carried on without further purification.

acetate then dissolved in 5:1 CHCl$_3$:CF$_3$CH$_2$OH and washed with 0.5M NaHSO$_4$, saturated aqueous NaHCO$_3$, and saturated aqueous NaCl solutions. A solid precipitated upon addition of the aqueous solutions. This solid was isolated by filtration and dried under vacuum to give a white solid (Boc-(γ-ACPC)$_6$-OBn, JKMI155, approximately 0.1 g). $^1$H NMR (300 MHz, 5:1 CD$_2$Cl$_2$:CF$_3$CD$_2$OD): δ=7.37–7.34 (m, 5H), 6.95–6.82 (br. m, 4H), 6.65 (d, J=6.0 Hz, 1H), 5.15 (s, 1H), 5.10 (s, 2H), 3.93–3.89 (m, 2H), 3.88–3.58 (m, 3H), 3.59–3.40 (m, 11H), 2.57 (dd, J=15.6, 4.9 Hz, 1H), 2.36–2.26 (m, 3H), 2.13–1.83 (m, 15H), 1.70–1.63 (m, 8H), 1.41–1.18 (m, 26H) ppm. MALDI-TOF MS: m/z=981.5 {M+Na}$^+$.

{(1R,2S)-2-(9H-Fluoren-9-ylmethoxycarbonylamino)-cyclopentyl}-acetic acid (Fmoc-γ-ACPC-OH): (1S,2S)-2-

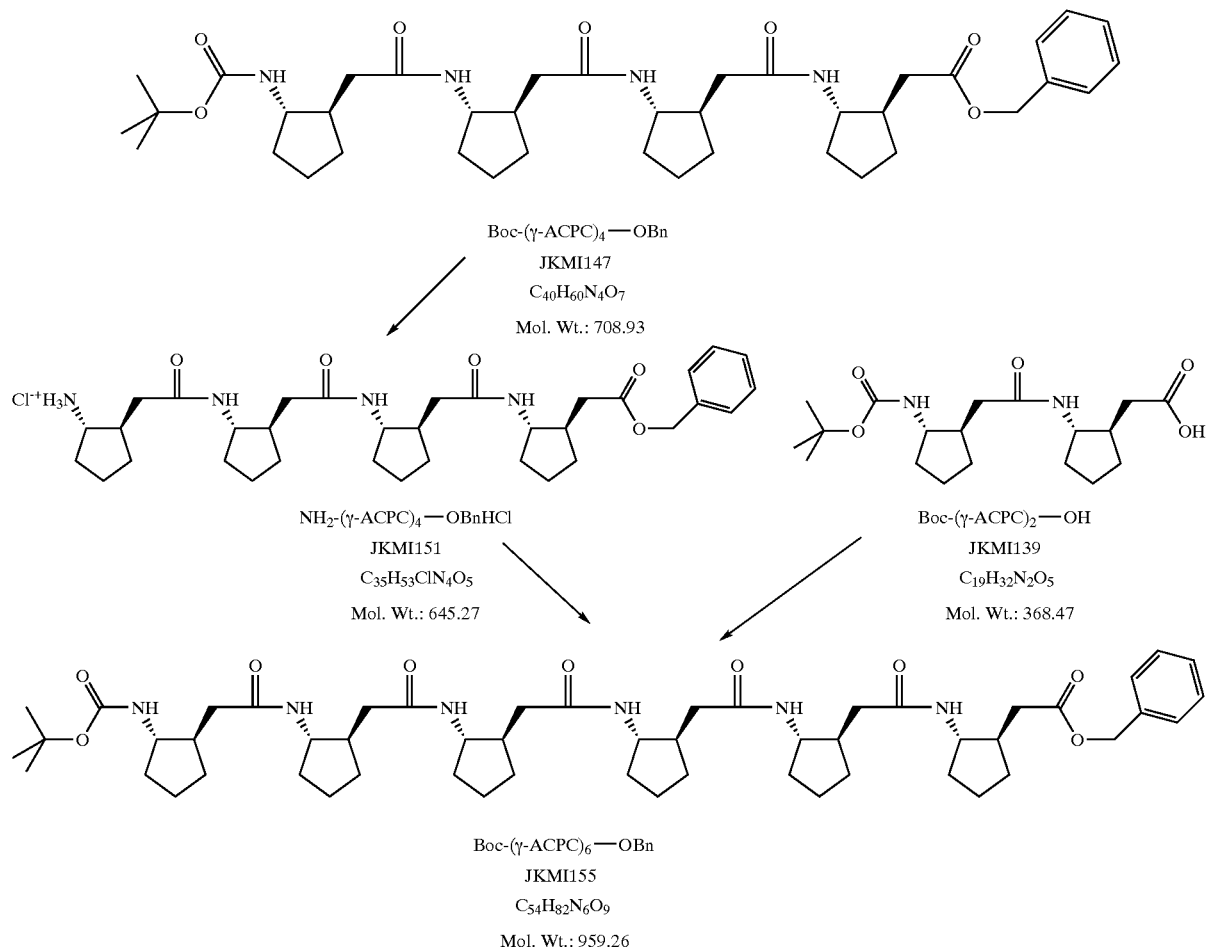

Scheme 7

Boc-(γ-ACPC)$_4$—OBn
JKMI147
C$_{40}$H$_{60}$N$_4$O$_7$
Mol. Wt.: 708.93

NH$_2$-(γ-ACPC)$_4$—OBnHCl
JKMI151
C$_{35}$H$_{53}$ClN$_4$O$_5$
Mol. Wt.: 645.27

Boc-(γ-ACPC)$_2$—OH
JKMI139
C$_{19}$H$_{32}$N$_2$O$_5$
Mol. Wt.: 368.47

Boc-(γ-ACPC)$_6$—OBn
JKMI155
C$_{54}$H$_{82}$N$_6$O$_9$
Mol. Wt.: 959.26

Boc-γ-(ACPC)$_2$-OH (JKMI139, 0.078 g, 0.212 mmol), NH$_2$-(γ-ACPC)$_4$-OBn•HCl (JKMI151), and 4-dimethylaminopyridine (0.091 g, 0.742 mmol) were dissolved in DMF (5 mL, anhydrous). To the solution was added 1-(3-dimethylaminopropyl)-3-ethylcarbodiimide hydrochloride (0.061 g, 0.318 mmol), and the reaction mixture was stirred under N$_2$ at room temperature for 48 h. The solvent was then removed under a stream of N$_2$ and then under high vacuum. The residue was diluted with H$_2$O. The insoluble material was isolated by filtration and dried under vacuum. This solid was washed with diethyl ether and ethyl (9H-Fluoren-9-ylmethoxycarbonylamino)-cyclopentane carboxylic acid (See See LePlae, Umezawa, Lee & Gellman (2001) J. Org. Chem. 66:5629–5632) (Fmoc-ACPC-OH, JKMI97, 0.56 g, 1.59 mmol) was placed in an oven-dried flask with a clear-seal joint containing an oven-dried stir bar and dissolved in dry THF (8 mL) under a N$_2$ atmosphere. The solution was cooled to −14° C. with an ice/brine bath. N-methylmorpholine (183 μL, 1.67 mmol) and isobutylchloroformate (216 μL, 1.67 mmol) were added via syringe. The mixture was stirred for 1 h and allowed to warm to 0° C. A white precipitate formed during this time. The flask was then fitted with an oven-dried "Diazald"-brand apparatus, and the joint was sealed with parafilm. A solution of KOH (4 g, 71.4 mmol) in H$_2$O (6.7 mL) and 2-methoxyethanol (5.3 mL) was placed in the well of the apparatus with a stir bar and heated to 75° C. A saturated solution of "Diazald" reagent (1.02 g, 4.76 mmol) in diethyl ether (10 mL) was decanted into a dropping funnel attached to the apparatus. The vacuum adapter was fitted with a septum, and the system was placed under N$_2$. The cold finger was cooled to −78° C. with a dry ice/isopropanol mixture. The "Diazald" solution was then dropped into the KOH solution over a period of 30 min. The yellow diazomethane distilled over, condensed on the cold finger, and dropped into the reaction mixture. Once distillation of the diazomethane was complete, and the reaction mixture had a persistent yellow color, the "Diazald" apparatus was removed. The flask was stoppered, placed under N$_2$, and stirred for four h, being allowed to warm from 0° C. to room temperature. Acetic acid (1 mL) was then added to neutralize any excess diazomethane. An off-white precipitate formed at this time. The reaction mixture was diluted with CH$_2$Cl$_2$ (200 mL), washed with saturated aqueous NaHCO$_3$ (2×100 mL), aqueous HCl (1N, 100 mL) and saturated aqueous NaCl solution (100 mL). The organic layer was dried over MgSO$_4$, filtered, and concentrated. The crude product was purified by column chromatography (1% methanol in CH$_2$Cl$_2$, loaded by adsorption onto silica gel) to give a white solid (Fmoc-ACPC-CHN$_2$, JKMI113, 0.42 g, 71%). $^1$H NMR (250 MHz, DMSO-d$_6$): δ=7.89 (d, J=7.0 Hz, 2H), 7.68 (d, J=7.3 Hz, 2H), 7.41 (t, j=7.4 Hz, 2H), 7.32 (t, J=7.4 Hz, 2H), 6.01 (s, 1H), 4.32–4.17 (m, 2H), 4.01–3.92 (m, 1H), 3.56–3.26 (m, 2H), 2.74–2.55 (m, 1H), 1.99–1.43 (m, 6H) ppm.

This solid (Fmoc-ACPC-CHN$_2$, JKMI113, 0.145 g, 0.387 mmol) was dissolved in water/dioxane (1/5, 20 mL), and the flask was covered in aluminum foil to exclude light. Silver benzoate (9 mg, 10 mol %) was added as a catalyst, and the mixture was sonicated at room temperature under N$_2$ for 1 h. At 0° C. the solution was acidified to pH 2 with aqueous HCl (1N). The solution was extracted with diethyl ether (4×25 mL). The organic layer was dried over MgSO$_4$, filtered, and concentrated to give a white solid. The crude product was purified by column chromatography (1:1:0.3 hexane:ethyl acetate:acetic acid). Acetic acid was removed on the high-vacuum rotary evaporator. Benzene (2×100 mL) was added and removed on the rotary evaporator. The residue was recrystallized from CH$_2$Cl$_2$/hexane to obtain a white solid (Fmoc-γ-ACPC-OH, JKMI115, 0.041 g, 29%). $^1$H NMR (300 MHz, CD$_3$OD): δ=7.78 (d, J=7.3 Hz, 2H), 7.64 (d, J=7.5 Hz, 2H), 7.38 (t, j=7.3 Hz, 2H), 7.30 (t, J=7.4 Hz, 2H), 4.41–4.31 (m, 2H), 4.21 (t, J=6.7 Hz, 1H), 3.54 (q, J=8.0 Hz, 1H), 2.51 (dd, J=14.6, 3.3 Hz, 1H), 2.19–1.93 (m, 5H), 1.72–1.25 (m, 5H) ppm.

(3S,4R)-3-Carboxymethyl-4-(9H-fluoren-9-ylmethoxycarbonylamino)-pyrrolidine-1-carboxylic acid tert-butyl ester (Fmoc-γ-APC(Boc)-OH): (4R,3S)-4-(9H-Fluoren-9-ylmethoxycarbonylamino)-pyrrolidine-1,3-dicarboxylic acid 1-tert-butyl ester (see Lee, LePlae, Porter & Gellman (2001) *J. Org. Chem.* 66:3597–3599) (Fmoc-APC(Boc)-OH, JKMI299, 5.05 g, 11.2 mmol) was placed in an oven-dried flask with a clear-seal joint containing an oven-dried stir bar and dissolved in dry THF (22 mL) under a N$_2$ atmosphere. The solution was cooled to −14° C. with an ice/brine bath. N-methylmorpholine (1.29 mL, 11.7 mmol) and isobutylchloroformate (1.52 mL, 11.7 mmol) were added via syringe. The mixture was stirred for 1 h and allowed to warm to 0° C. A white precipitate formed during this time. The flask was then fitted with an oven-dried "Diazald" apparatus, and the joint was sealed with parafilm. A solution of KOH (4.8 g, 85.7 mmol) in H$_2$O (8.0 mL) and 2-methoxyethanol (6.4 mL) was placed in the well of the apparatus with a stir bar and heated to 75° C. A saturated solution of "Diazald" reagent (7.2 g, 33.5 mmol) in diethyl ether (40 mL) was decanted into a dropping funnel attached to the apparatus. The vacuum adapter was fitted with a septum, and the system was placed under N$_2$. The cold finger was cooled to −78° C. with a dry ice/isopropanol mixture. The "Diazald" solution was then dropped into the KOH solution over a period of 30 min. The yellow diazomethane distilled over, condensed on the cold finger, and dropped into the reaction mixture. Once distillation of the diazomethane was complete, and the reaction mixture had a persistent yellow color, the "Diazald" apparatus was removed. The flask was stoppered, placed under N$_2$, and stirred for 4 h, being allowed to warm from 0° C. to room temperature. Acetic acid (1 mL) was then added to neutralize any excess diazomethane. The reaction mixture was diluted with diethyl ether (200 mL), washed with saturated aqueous NaHCO$_3$ (2×100 mL), aqueous HCl (1N, 100 mL), and saturated aqueous NaCl solution (100 mL). The organic layer was dried over MgSO$_4$, filtered, and concentrated. The crude product was purified by column chromatography (1:1 hexane:ethyl acetate) to give a pale yellow solid (Fmoc-APC(Boc)-CHN$_2$, JKMII7, 4.44 g, 84%). This compound exists as slowly interconverting rotamers. $^1$H NMR (300 MHz, CDCl$_3$): δ=7.82 (d, J=7.3 Hz, 2H), 7.59 (d, J=7.3 Hz, 2H), 7.42 (t, j=7.2 Hz, 2H), 7.33 (t, J=7.3 Hz, 2H), 5.60, 5.54 (br. s, 1H), 5.18, 5.12 (br. s, 1H), 4.80–4.47 (br. m, 3H), 4.22 (d, J=6.4 Hz, 2H), 3.72–2.99 (br. m, 5H), 1.71 (s, 1H), 1.47 (s, 9H) ppm.

This solid (Fmoc-APC(Boc)-CHN$_2$, JKMII7, 4.44 g, 9.33 mmol) was dissolved in water/dioxane (1/5, 467 mL), and the flask was covered in aluminum foil to exclude light. Silver benzoate (0.214 g, 10 mol %) was added as a catalyst, and the mixture was sonicated at room temperature under N$_2$ for 1 h. At 0° C. the solution was acidified to pH 2 with aqueous 0.5M NaHSO$_4$. The solution was extracted with diethyl ether (4×200 mL). The organic layer was dried over MgSO$_4$, filtered, and concentrated to give a white solid. The crude product was purified by column chromatography (1:1:0.3 hexane:ethyl acetate:acetic acid). Acetic acid was removed on the high vacuum rotary evaporator. Benzene (2×100 mL) was added and removed on the rotary evaporator. The residue was dried under high vacuum overnight to give a white solid (Fmoc-γ-APC(Boc)-OH, JKMII9, 2.61 g, 60%). This compound exists as slowly interconverting rotamers. $^1$H NMR (300 MHz, CD$_3$OD): δ=7.77 (d, J=7.5 Hz, 2H), 7.63 (d, J=7.4 Hz, 2H), 7.37 (t, j=7.0 Hz, 2H), 7.30 (t, J=7.6 Hz, 2H), 4.42–4.36 (m, 2H), 4.16 (t, J=6.5 Hz, 1H), 3.86–3.80 (m, 1H), 3.74–3.63 (m, 2H), 3.06–3.00 (m, 2H), 2.53 (dd, J=15.7, 3.6 Hz, 1H), 2.42–2.22 (m, 2H), 1.45 (s, 9H) ppm.

Ac-(γ-APC-γ-ACPC)$_3$-NH$_2$: The γ-peptide Ac-(γ-APC-γ-ACPC)$_3$-NH$_2$ was synthesized from Fmoc-γ-APC(Boc)-OH (JKMII9) and Fmoc-γ-ACPC-OH (JKMI115) on a 25-μmol scale by standard methods on Rink amide AM resin (Applied Biosystems, Foster City, Calif.), using a Synergy automated synthesizer (Applied Biosystems). Amino acid (3 equiv.), HBTU (3 equiv.), and Scheme 8
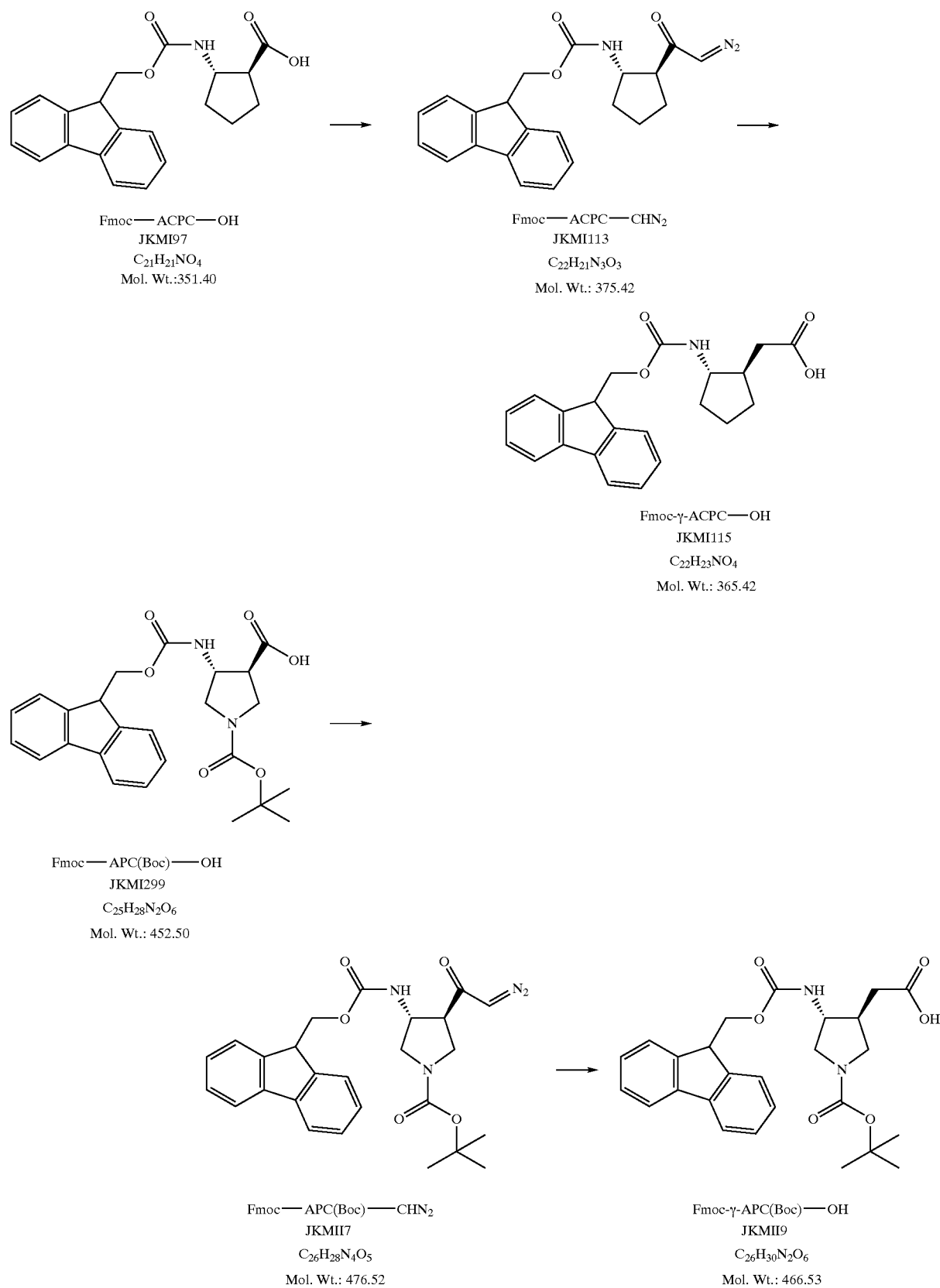

-continued

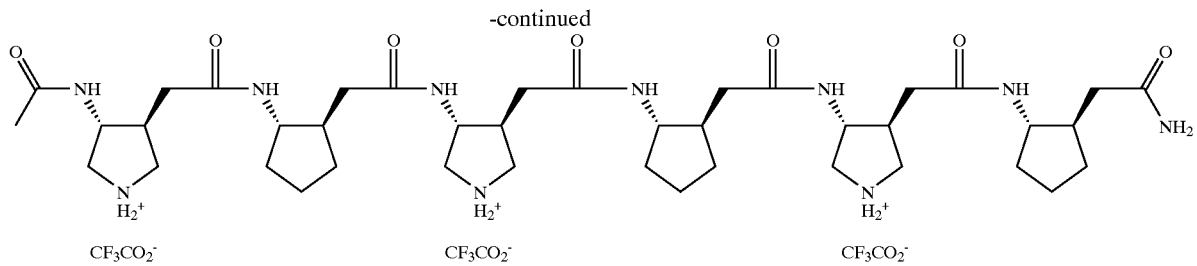

Ac-(γ-APC-γ-ACPC)—NH₂ as TFA Salt

JKMII23

C₄₇H₇₁F₉N₁₀O₁₃

Mol. Wt.: 1155.11

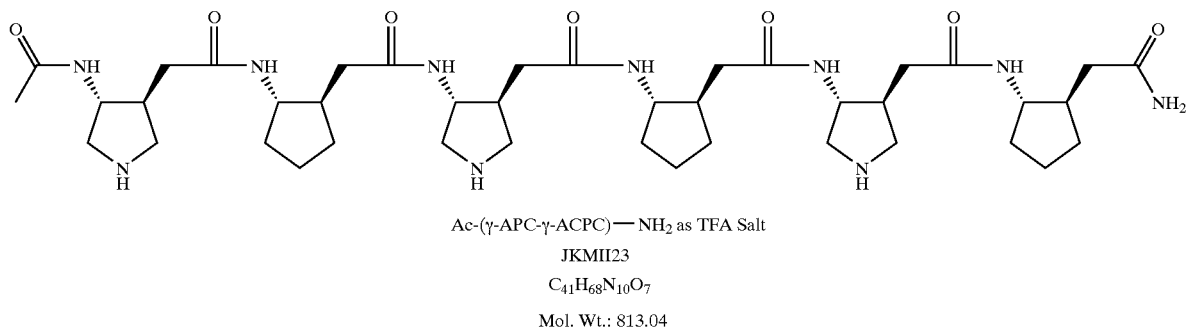

Ac-(γ-APC-γ-ACPC)—NH₂ as TFA Salt

JKMII23

C₄₁H₆₈N₁₀O₇

Mol. Wt.: 813.04

DIEA (6 equiv.) were used in each coupling cycle. Coupling cycles were 120 min. in duration, and piperdine deprotection cycles were approximately 60 min. in duration (actual deprotection time was regulated automatically by monitoring the conductivity trace). The resin-bound γ-peptide was cleaved and simultaneously deprotected by using 2 mL of 19:1 trifluoroacetic acid/H$_2$O and stirring for 4 h. The mixture was filtered through glass wool to remove the resin, and the filtrate was added to 7 mL of cold, anhydrous diethyl ether. The precipitate was collected by centrifugation. The γ-peptide was purified by reverse-phase HPLC on a C$_{18}$-silica semi-preparative column (5 μm; 10 mm×250 mm; Vydac, Hesperia, Calif.). The column was eluted with a gradient of acetonitrile in water (8–32%; 0.1% trifluoroacetic acid in each) at a flow rate of 5 mL/min. Collected fractions were pooled and lyophilized to produce a white powder (Ac-(γ-APC-γ-ACPC)$_3$-NH$_2$, JKMII23). $^1$H NMR (500 MHz, CD$_3$OH): δ=8.54–8.51 (m, 2H), 8.46 (d, J=7.1 Hz, 1H), 8.25–8.19 (m, 3H), 7.79 (s, 1H), 6.95 (s, 1H), 4.21–4.16 (m, 2H), 3.83–3.78 (m, 3H), 3.70–3.60 (m, 6H), 3.16–3.04 (m, 6H), 2.57–2.51 (m, 6H), 2.41–2.31 (m, 6H), 2.17–1.89 (m, 16H), 1.74–1.63 (m, 6H), 1.54–1.47 (m, 3H), 1.45–1.36 (m, 3H) ppm. MALDI-TOF MS: calcd. for C$_{41}$H$_{68}$N$_{10}$O$_7$ {M} 812.5, found 813.4 {M+H}$^+$, 835.3 {M+Na}$^+$, 851.3 {M+K}$^+$.

((1S,2R)-2-tert-Butoxycarbonylamino-cyclohexyl)-acetic acid (Boc-γ-ACHC-OH): (1R,2R)-2-Amino-cyclohexanecarboxylic acid (see Schinnerl, Murray, Langenhan, & Gellman (2003) *Eur. J. Org. Chem.* 721–726) (NH$_2$-ACHC-OH, JKMI223, 2.18 g, 15.2 mmol) was dissolved in methanol (152 mL). Triethylamine (4.33 mL, 31.15 mmol) was added via syringe followed by di-tert-butyl-dicarbonate (3.41 g, 15.65 mmol). The reaction mixture was stirred at room temperature for 2 h. The solvent was removed by rotary evaporation. The residue was diluted with ethyl acetate (200 mL), washed with 0.5M NaHSO$_4$ (1×100 mL) and saturated aqueous NaCl solution (1×100). The organic layer was dried over MgSO$_4$, filtered, and concentrated to give a white solid. The crude product was purified by column chromatography (6:4:0.3) hexane:ethyl acetate:acetic acid). Acetic acid was removed on the high vacuum rotary evaporator. Benzene (2×100 mL) was added and removed on the rotary evaporator. The residue was dried under high vacuum overnight to give a white solid (Boc-ACHC-OH, JKMI229, 2.52 g, 68%). $^1$H NMR (250 MHz, CDCl$_3$): δ=10.46 (br. s, 1H), 5.97 (br. s, 1H), 4.61 (br. s, 1H), 3.64 (br. s, 1H), 2.25 (td, J=11.3, 3.6, 2H), 2.08–1.95 (m, 4H), 1.75–1.16 (m, 11H) ppm.

(1S, 2S)-2-tert-Butoxycarbonylamino-cyclohexanecarboxylic acid (Boc-ACHC-OH, JKMI229, 3.61 g, 14.9 mmol) was placed in an oven-dried flask with a clear-seal joint containing an oven-dried stir bar and dissolved in dry THF (30 mL) under a N$_2$ atmosphere. The solution was cooled to −14° C. with an ice/brine bath. N-methylmorpholine (1.72 mL, 15.6 mmol) and isobutylchloroformate (2.02 mL, 15.6 mmol) were added via syringe. The mixture was stirred for 1 h and allowed to warm to 0° C. A white precipitate formed during this time. The flask was then fitted with an oven-dried "Diazald" apparatus, and the joint was sealed with parafilm. A solution of KOH (6 g, 107 mmol) in H$_2$O (10 mL) and 2-methoxyethanol (8 mL) was placed in the well of the apparatus with a stir bar and heated to 75° C. A saturated solution of "Diazald" reagemt (9.56 g, 44.6 mmol) in diethyl ether (50 mL) was decanted into a dropping funnel attached to the apparatus. The vacuum adapter was fitted with a septum, and the system was placed under N$_2$. The cold finger was cooled to −78° C. with a dry ice/isopropanol mixture. The "Diazald" solution was then dropped into the KOH solution over a period of 30 min. The yellow diazomethane distilled over, condensed on the cold finger, and dropped into the reaction mixture. Once distillation of the diazomethane was complete, and the reaction mixture had a persistent yellow color, the "Diazald" apparatus was removed. The flask was stoppered, placed under $N_2$, and stirred for 4 h, being allowed to warm from 0° C. to room temperature. Acetic acid (1 mL) was then added to neutralize any excess diazomethane. The reaction mixture was diluted with diethyl ether (200 mL), washed with saturated aqueous $NaHCO_3$ (2×100 mL), aqueous HCl (1N, 100 mL), and saturated aqueous NaCl solution (100 mL). The organic layer was dried over $MgSO_4$, filtered, and concentrated. The crude product was purified by column chromatography (6:4 hexane:ethyl acetate) to give a pale yellow solid (Boc-ACHC-CHN$_2$, JKMI241, 1.24 g, 31%). $^1$H NMR (300 MHz, CDCl$_3$): δ=5.45 (s, 1H), 4.66 (d, J=8.4 Hz, 1H), 3.54–3.50 (m, 1H), 2.35 (br. s, 1H), 2.04–1.73 (m, 5H), 1.51–1.17 (m, 12H) ppm.

This solid (Boc-ACHC-CHN$_2$, JKMI241, 1.24 g, 4.63 mmol) was dissolved in water/dioxane (1/5, 231 mL), and the flask was covered in aluminum foil to exclude light. Silver benzoate (0.106 g, 10 mol %) was added as a catalyst, and the mixture was sonicated at room temperature under $N_2$ for 1 h. At 0° C., the solution was acidified to pH 2 with aqueous 0.5M $NaHSO_4$. The solution was extracted with diethyl ether (4×150 mL). The organic layer was dried over $MgSO_4$, filtered, and concentrated to give a white solid. The crude product was purified by column chromatography (6:4:0.3 hexane:ethyl acetate:acetic acid). Acetic acid was removed on the high-vacuum rotary evaporator. Benzene (2×150 mL) was added and removed on the rotary evaporator to give a white solid (Boc-γ-ACHC-OH, JKMI243, 1.273 g, wet). $^1$H NMR (300 MHz, CDCl$_3$): δ=10.52 (br. s, 1H), 4.58 (d, J=9.7 Hz, 1H), 3.41–3.11 (m, 2H), 2.60 (dd, J 15.4, 5.5, Hz, 1H), 2.35–2.11 (m, 2H), 2.01–1.74 (m, 6H), 1.58–1.09 (m, 10H) ppm. MS-ESI: m/z=280.1 {M+Na}$^+$, 537.2 {2M+Na}$^+$, 256.1 {M–H}$^-$, 513.3 {2M–H}$^-$.

Scheme 9

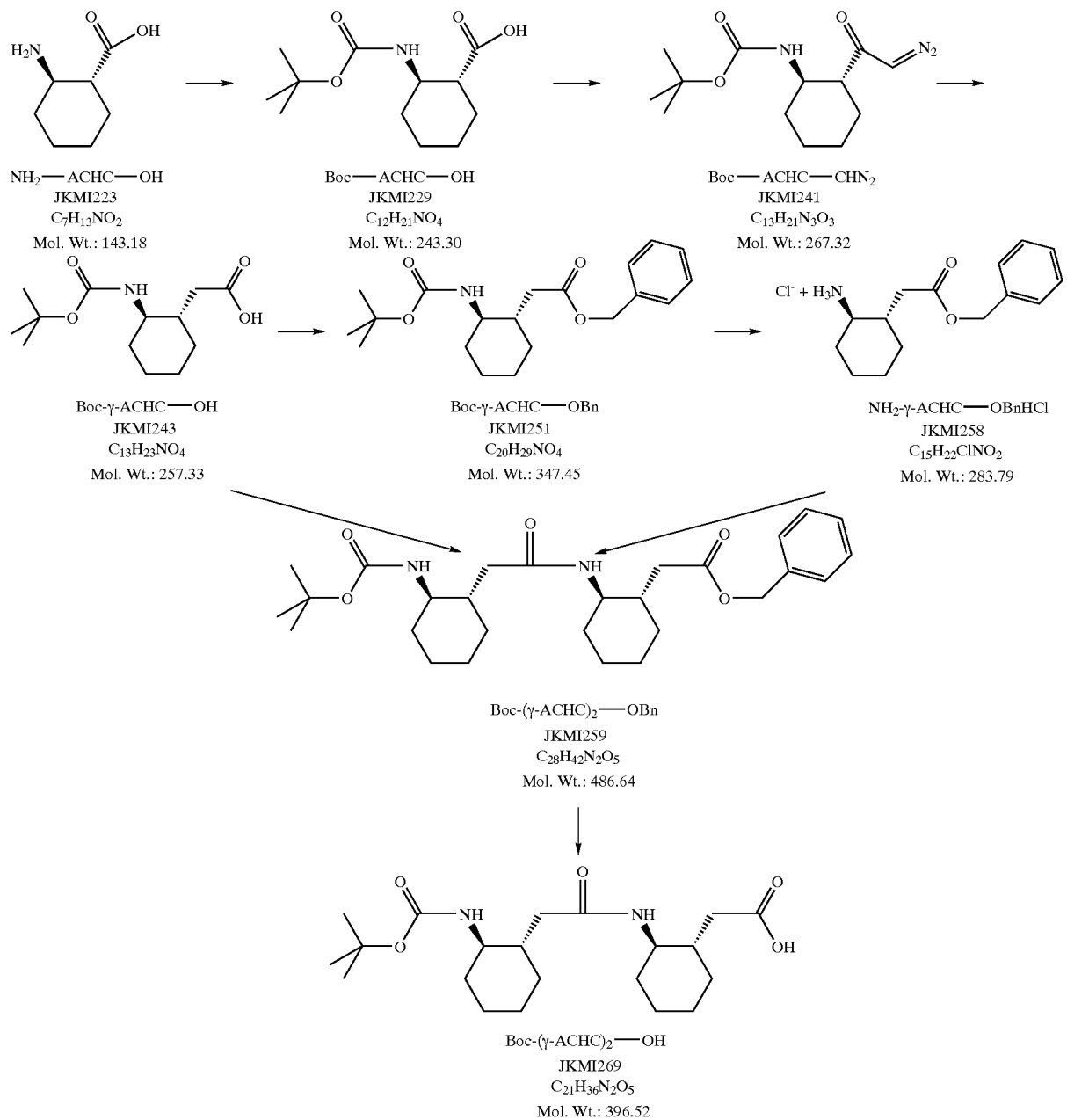

((1R,2S)-2-tert-Butoxycarbonylamino-cyclohexyl)-acetic acid (Boc-γ-ACHC-OH, JKMI195) was prepared by starting with (1S,2S)-2-amino-cyclohexanecarboxylic acid (NH$_2$-ACHC-OH, JKMI181), see Schinnerl, Murray, Langenhan & Gellman (2001) *Eur. J. Org. Chem.* 721–726.

Boc-(γ-ACHC)$_2$-OH: This solid (Boc-γ-ACHC-OH, JKMI243, 0.30 g, 1.17 mmol) and CsCO$_3$ (0.40 g, 1.23 mmol) were dissolved in DMF (11.7 mL, anhydrous). Benzyl bromide (0.15 mL, 1.26 mmol) was added, and the mixture was stirred at room temperature under N$_2$ covered in aluminum foil for 24 h. The mixture was diluted with ethyl acetate (100 mL) and washed with saturated aqueous NaHCO$_3$ (1×50 mL) and saturated aqueous NaCl (1×50 mL) solutions. The organic layer was dried over MgSO$_4$, filtered, and concentrated to give a white solid. The crude product was purified by column chromatography (8.5:1.5 hexane:ethyl acetate) and dried overnight under high vacuum to give white solid (Boc-γ-ACHC-OBn, JKMI251, 0.34 g, 87%). $^1$H NMR (300 MHz, CDCl$_3$): δ=7.40–7.27 (m, 5H), 5.12 (AB quar., $v_a$=5.14, $v_b$=5.09, $J_{ab}$=12.5 Hz, 2H), 4.49 (2, J=9.6 Hz, 1H), 3.27–3.17 (m, 1H), 2.64 (dd, J=15.8, 5.0 Hz, 1H), 2.21–1.95 (m, 3H), 1.83–1.63 (m, 4H), 1.48–1.10 (m, 12H) ppm.

This white solid (Boc-γ-ACHC-OBn, JKMI251, 0.202 g, 0.608 mmol) was dissolved in 4N HCl in dioxane (5 mL) and stirred under N$_2$ for three hours at room temperature. The solvent was blown off overnight under a stream of N$_2$. The residue was placed under high vacuum for one hour and then carried on without further purification (NH$_2$-γ-ACHC-OBn•HCl, JKMI258).

Boc-γ-ACHC-OH (JKM243, 0.156 g, 0.608 mmol), NH$_2$-γ-ACHC-OBn•HCl (JKMI258, 0.608 mmol), and 4-dimethylaminopyridine (0.222 g, 1.82 mmol) were dissolved in DMF (3.64 mL, anhydrous). To the solution was added 1-(3-dimethylaminopropyl)-3-ethylcarbodiimide hydrochloride (0.175 g, 0.912 mmol), and the reaction mixture was stirred under N$_2$ at room temperature overnight. The mixture was diluted with 50 mL ethyl acetate and washed with 0.5 M aqueous NaHSO$_4$ (1×50 mL), saturated aqueous NaHCO$_3$ (1×50 mL), and saturated aqueous NaCl (1×50 mL) solutions. The organic layer was dried over MgSO$_4$, filtered, and concentrated. The crude product was purified by column chromatography (1:1 hexane:ethyl acetate) to give a white solid (Boc-(γ-ACHC)$_2$-OBn, JKMI259, 0.224 g, 76%). $^1$H NMR (300 MHz, CDCl$_3$): δ=7.36–7.27 (m, 5H), 5.94 (d, J=8.8 Hz, 1H), 5.11 (s, 2H), 4.63 (d, J=9.2 Hz, 1H), 3.60–3.50 (m, 1H), 3.20–3.10 (m, 1H), 2.54 (dd, J=16.3, 5.2, 1H), 2.30–2.14 (m, 2H), 2.03–1.59 (m, 12H), 1.48–0.95 (m, 16H).

Boc-(γ-ACHC)$_2$-OBn (JKMI259, 0.0875 g, 0.180 mmol) was dissolved in methanol (1.8 mL), and the flask was flushed with N$_2$. To the flask was added Pd/C 10% (0.013 g), and the flask was attached to a Parr apparatus and shaken overnight at an H$_2$ pressure of 44 psi. The reaction mixture was filtered through a syringe filter and concentrated on a rotary evaporator to give a white solid (Boc-(γ-ACHC)$_2$-OH, JKMI269). MS-ESI: m/z=397.2 {M+H}$^+$, 419.2 {M+Na}$^+$.

{(1R,2S)-2-(9H-Fluoren-9-ylmethoxycarbonylamino)-cyclohexyl}-acetic acid (Fmoc-g-ACHC-OH): Boc-γ-ACHC-OH (JKMI195, 1.20 g, 4.95 mmol) was dissolved in 4N HCl in dioxane (10 mL) and stirred under N$_2$ for three hours at room temperature. The solvent was blown off overnight under a stream of N$_2$. The residue was placed under high vacuum for one hour and then carried on without further purification (NH$_2$-γ-ACHC-OH, JKMII13).

This residue (NH$_2$-γ-ACHC-OH•HCl, JKMII13, 4.95 mmol), was dissolved in acetone/H$_2$O (250 mL, 2:1) and cooled to 0° C., and Fmoc-OSu (1.67 g, 4.95 mmol) and NaHCO$_3$ (4.58 g, 54.5 mmol) were added. The turbid reaction mixture was stirred at 0° C. for 1 h and was then allowed to stir at room temperature for 12 h. The acetone was removed by rotary evaporation. The aqueous residue was diluted with H$_2$O (100 mL), and stirred at room temperature with diethyl ether (150 mL) for 1 h. The layers were separated, and the organic layer was washed with saturated aqueous NaHCO$_3$ (3×50 mL). The organic layer was discarded, and all the aqueous layers were combined, acidified with 1N aqueous HCl, and extracted with ethyl acetate (3×10 mL). The organic extracts were dried over MgSO$_4$, filtered, and concentrated to obtain a white solid. The crude product was purified by column chromatography (1:1:0.3 hexanes:ethyl acetate:acetic acid) and recrystallized from CHCl$_3$/hexanes to give a white powder (Fmoc-γ-ACHC-OH, JKMII15, 0.924 g, 49%). $^1$H NMR (300 MHz, CD$_3$OD): δ=7.77 (d, J=7.4 Hz, 2H), 7.58 (d, J=7.2 Hz, 2H), 7.37 (t, j=7.6 Hz, 2H), 7.28 (t, J=7.5 Hz, 2H), 4.57–4.15 (m, 3H), 3.70–3.64 (m, 1H), 3.18–3.11 (m, 1H), 2.48 (dd, J=15.4, 3.8, 1H), 2.39–2.30 (m, 1H), 1.73–1.15 (m, 9H) ppm.

(3S,4S)-3-Carboxymethyl-4-(9H-fluoren-9-ylmethoxycarbonylamino)-piperidine-1-carboxylic acid tert-butyl ester (Fmoc-γ-APiC(Boc)-OH): (3S,4S)-4-(9H-Fluoren-9-ylmethoxycarbonylamino)-piperidine-1,3-dicarboxylic acid 1-tert-butyl ester (LePlae, Umezawa, Lee & Gellman, supra) (Fmoc-APiC(Boc)-OH, JKMII29, 0.37 g, 0.79 mmol) was placed in an oven-dried flask with a clear-seal joint containing an oven-dried stir bar and dissolved in dry THF (4 mL) under a N$_2$ atmosphere. The solution was cooled to −14° C. with an ice/brine bath. N-methylmorpholine (92 μL, 0.83 mmol) and isobutylchloroformate (0.108 μL, 0.83 mmol) were added via syringe. The mixture was stirred for 1 h and allowed to warm to 0° C. A white precipitate formed during this time. The flask was then fitted with an oven-dried "Diazald"-brand apparatus, and the joint was sealed with parafilm. A solution of KOH (4 g, 71.4 mmol) in H$_2$O (6.7 mL) and 2-methoxyethanol (5.3 mL) was placed in the well of the apparatus with a stir bar and heated to 75° C. A saturated solution of "Diazald" reagent (0.51 g, 2.38 mmol) in diethyl ether (8 mL) was decanted into a dropping funnel attached to the apparatus. The vacuum adapter was fitted with a septum, and the system was placed under N$_2$. The cold finger was cooled to −78° C. with a dry ice/isopropanol mixture. The "Diazald" solution was then dropped into the KOH solution over a period of 30 min. The yellow diazomethane distilled over, condensed on the cold finger, and dropped into the reaction mixture.

Once distillation of the diazomethane was complete, and the reaction mixture had a persistent yellow color, the "Diazald" apparatus was removed. The flask was stoppered, placed under N$_2$, and stirred for 4 h, being allowed to warm from 0° C. to room temperature. Acetic acid (0.5 mL) was then added to neutralize any excess diazomethane. The reaction mixture was diluted with diethyl ether (100 mL), washed with saturated aqueous NaHCO$_3$ (2×50 mL), aqueous HCl (1N, 50 mL), and saturated aqueous NaCl solution (50 mL). The organic layer was dried over MgSO$_4$, filtered, and concentrated. The crude product was purified by column chromatography (1:1 hexane:ethyl acetate) to give a pale yellow solid (Fmoc-APiC(Boc)-CHN$_2$, JKMII37, 0.154 g, 40%). $^1$H NMR (300 MHz, CDCl$_3$): δ=7.73 (d, J=7.4 Hz, 2H), 7.56 (d, J=7.5 Hz, 2H), 7.37 (t, j=7.0 Hz, 2H), 7.28 (t, J=7.4 Hz, 2H), 5.48 (br. d, J=6.7 Hz, 1H), 4.36–3.93 (m, 7H), 3.20–2.60 (m, 2H), 2.10–1.90 (m, 3H), 1.46 (s, 9H) ppm.

This solid (Fmoc-APiC(Boc)-CHN$_2$, JKMII37, 0.154 g, 0.314 mmol) was dissolved in water/dioxane (1/5, 18 mL), and the flask was covered in aluminum foil to exclude light. Silver benzoate (7.2 mg, 10 mol %) was added as a catalyst, and the mixture was sonicated at room temperature under N$_2$ for 1 h. At 0° C., the solution was acidified to pH 2 with aqueous 0.5M NaHSO$_4$. The solution was extracted with diethyl ether (4×25 mL). The organic layer was dried over MgSO$_4$, filtered, and concentrated to give a white solid. The crude product was purified by column chromatography (7:3:0.3 hexane:ethyl acetate:acetic acid). Acetic acid was removed on the high-vacuum rotary evaporator. Benzene (2×100 mL) was added and removed on the rotary evaporator. The residue was dried under high vacuum overnight to give a white solid (Fmoc-g-APiC(Boc)-OH), JKMII47, 0.060 g, 40%). $^1$H NMR (300 MHz, CDCl$_3$): δ=7.75 (d, J=6.5 Hz, 2H), 7.57 (d, J=6.2 Hz, 2H), 7.39 (t, j=7.4 Hz, 2H), 7.30 (t, J=7.0 Hz, 2H), 4.80–3.90 (m, 7H), 3.65 (br. s, 1H), 2.79 (br. s, 1H), 2.60–2.30 (br, m, 1H), 2.30–1.90 (br. m, 4H), 1.44 (s, 10H) ppm.

Scheme 10

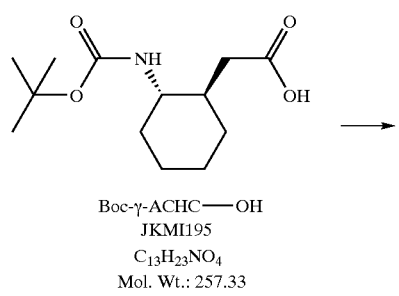

Boc-γ-ACHC—OH
JKMI195
C$_{13}$H$_{23}$NO$_4$
Mol. Wt.: 257.33

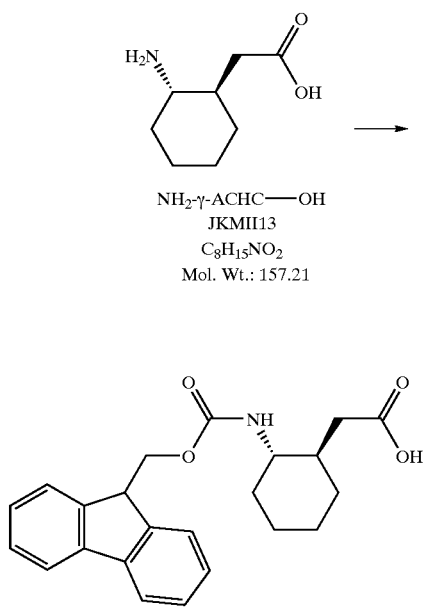

NH$_2$-γ-ACHC—OH
JKMII13
C$_8$H$_{15}$NO$_2$
Mol. Wt.: 157.21

Fmoc-γ-ACHC—OH
JKMII15
C$_{23}$H$_{25}$NO$_4$
Mol. Wt.: 379.45

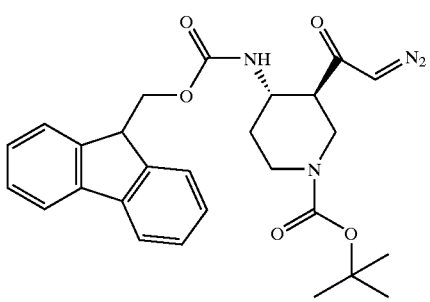

Fmoc—APiC(Boc)—OH
JKMII29
C$_{26}$H$_{30}$N$_2$O$_6$
Mol. Wt.: 466.53

Fmoc—APiC(Boc)—CHN$_2$
JKMII37
C$_{27}$H$_{30}$N$_4$O$_5$
Mol. Wt.: 490.55

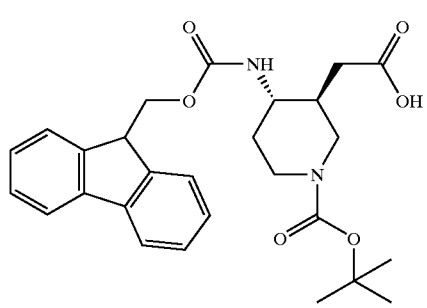

Fmoc-γ-APiC(Boc)—OH
JKMII47
C$_{27}$H$_{32}$N$_2$O$_6$
Mol. Wt.: 480.55

BIBLIOGRAPHY

Abele, Guichard, & Seebach (1998) "(S)-β$^3$-homolysine- and (S)-β$^3$-homoserine-containing β-peptides: CD spectra in aqueous solution," *Helv. Chim. Acta* 81:2141.

Appella, Christianson, Karle, Powell, & Gellman (1996) "β-Peptide Foldamers: Robust Helix Formation in a New Family of β-Amino Acid Oligomers," *J. Am. Chem. Soc.* 118:13071.

Appella, Christianson, Klein, Powell, Huang, Barchi, & Gellman (1997) "Residue-Based Control of Helix Shape in β-Peptide Oligomers *Nature* 387:381.

Appella, Christianson, Karle, Powell & Gellman (1999)$^a$ "Synthesis and Characterization of trans-2-Aminocyclohexanecarboxylic Acid Oligomers: An Unnatural Secondary Structure, and Implications for β-Peptide Tertiary Structure," *J. Am. Chem. Soc.* 121:6206.

Appella, Christianson, Klein, Richards, Powell, & Gellman (1999)$^b$ "Synthesis and Characterization of Helix-Forming γ-Peptides: trans-2-aminocyclopentanecarboxylic acid oligomers," *J. Am. Chem. Soc.* 121:7574.

Barchi, Huang, Appella, Christianson, Durell, & Gellman (2000) "Solution Conformations of Helix-Forming β-Amino Acid Homooligomers," *J. Am. Chem. Soc.* 122:2711.

Blaskovich, Lin, Delarue, Sun, Park, Coppola, Hamilton, & Sebti (2000) "Design of GFB-111, a platelet-derived growth factor binding molecule with antiangiogenic and anticancer activity against human tumors in mice," *Nature Biotechnol.* 18:1065.

Bolm, Schiffers, Dinter, & Gerlach (2000) "Practical and highly enantioselective ring opening of cyclic meso-anhydrides mediated by cinchona alkaloids," *J. Org. Chem.* 65:6984.

Bothner-By, Stephens, Lee, Warren, & Jeanloz R. W. (1984) *J. Am. Chem. Soc.* (1984) 106:811.

Braunschweiler & Ernst (1983) *J. Magn. Reson.* 53:521.

Cammers-Goodwin, Allen, Oslick, McClure, Lee, & Kemp (1996) "Mechanism of stabilization of helical conformations of polypeptides by water containing trifluoroethanol," *J. Am. Chem. Soc.* 118:3082.

Chin & Schepartz (2001) "Concerted evolution of structure and function in a miniature protein," *J. Am. Chem. Soc.* 123:2929.

Chung, Huck, Christianson, Stanger, Krauthauser, Powell & Gellman (2000) *J. Am. Chem. Soc.* 122:3995.

Cochran (2000) "Antagonists of protein-protein interactions," *Chem. Biol.* 7: R85.

Curran, Chandler, Kennedy, & Keaney (1996) "N-α-Benzoyl-cis-4-amino-L-proline: a γ-turn mimetic," *Tetrahedron Lett.* 37:1933.

Dado and Gellman (1994) *J. Am. Chem. Soc.* 116:1054–1062.

Fisk, Powell, & Gellman (2000) *J. Am. Chem. Soc.* 122:5443.

Degrado, Schneider, & Hamuro (1999) *Pept. Res.* 54:206.

Gellman (1998)$^a$ *Acc. Chem. Res.* 31:173.

Gellman (1998)$^b$ "Minimal model systems for β-sheet secondary structure in proteins," *Curr. Opin. Chem. Biol.* 2:717.

Gómez-Vidal & Silverman (2001) "Short, highly efficient syntheses of protected 3-azido- and 4-azidoproline and their precursors," *Org. Lett.* 3:2481.

Goodman, Verdini, Toniolo, Phillips, & Bovey (1969) *Proc. Natl. Acad. Sci. USA* 64:444.

Gung, Zou, Stalcup, & Cottrell, (1999) "Characterization of a water-soluble, helical β-peptide," *J. Org. Chem.* 64:2176.

Hamuro et al. (1999) *J. Am. Chem. Soc.* 121:12200–12201.

Hanessian, Luo, Schaum, Michnick (1998) "Design of secondary structures in unnatural peptides: stable helical γ-tetra-, hexa-, and octapeptides and consequences of α-substitution," *J. Am. Chem. Soc.* 120:8569.

Hanessian, Luo, Schaum (1999) Tetrahedron Lett. 40:4925.

Hintermann, Gademann, Jaun, Seebach (1998) "γ-Peptides forming more stable secondary structures than α-peptides: synthesis and helical NMR-solution structure of the γ-hexapeptide analog of H-(Val-Ala-Leu)$_2$-OH," *Helv. Chim. Acta* 81:983.

Kobayashi, Kamiyama, & Ohno (1990) "Chiral synthon obtained with pig-liver esterase-introduction of chiral centers into cyclohexene skeleton," *Chem. Pharm. Bull.* 38:350–354.

Kobayashi, Kamiyama, & Ohno (1990) "The first enantioselective synthesis of fortamine, the 1,4-diaminocyclitol moiety of fortimicin-A, by chemicoenzymatic approach," *J. Org. Chem.* 55:1169.

Lacroix, Kortemme, Lopez do la Paz, & Serrano (1999) *Curr. Opin. Struct. Biol.* 9:487.

Lee, Syud, Wang, Gellman (2001) "Diversity in Short β-Peptide 12-Helices: High Resolution Structural Analysis in Aqueous Solution of a Hexamer Containing Sulfonylated Pyrrolidine Residues," *J. Am. Chem. Soc.* 123:7721.

Luo & Baldwin (1997) "Mechanism of helix induction by trifluoroethanol: a framework for extrapolating the helix-forming properties of peptides from trifluoroethanol/water mixtures back to water," *Biochemistry* 36:8413.

Macura & Ernst (1980) *Mol. Phys.* 41:95.

Ragothama, Awasthi, Balaram, (1998) "β-Hairpin nucleation by Pro-Gly β-turns. Comparison of D-Pro-Gly and L-Pro-Gly sequences in an apolar octapeptide," *J. Chem. Soc., Perkin Trans.* 2:137.

Seebach et al. (1996)$^a$ *Helv. Chim. Acta.* 79:913–941.

Seebach et al. (1996)$^b$ *Helv. Chim. Acta.* 79:2043–2066.

Seebach & Matthews (1997) J. Chem. Soc., Chem. Commun. 2015–2022.

Seebach, Brenner, Rueping, Schweizer, Jaun (2001) "Preparation and determination of x-ray-crystal and NMR-solution structures of $\gamma^{2,3,4}$-peptides," *J. Chem. Soc., Chem. Commun.* 207.

Suhara et al. (1996) *Tetrahedron Lett.* 37(10):1575–1578

Walgers, Lee, & Cammers-Goodwin, (1998) "An indirect chaotropic mechanism for the stabilization of helix conformation of peptides in aqueous trifluoroethanol and hexafluoro-2-propanol," *J. Am. Chem. Soc.* 120:5073.

Wang, Liu, Zhang, Shan, Han, Srinivasula, Croce, Alnemri, & Huang (2000) "Structure-based discovery of an organic compound that binds Bcl-2 protein and induces apoptosis of tumor cells," *Proc. Natl. Acad. Sci. USA* 97:7124.

Woll, Lai, Guzei, Taylor, Smith, Gellman, "Parallel Sheet Secondary Structure in γ-Peptides," *J. Am. Chem. Soc.*, in press.

Zutshi, Brickner, & Chmielewski (1998) "Inhibiting the assembly of protein-protein interfaces," *Curr. Opin Chem. Biol.* 2:62.

What is claimed is:

1. An unnatural polypeptide compound selected from the group consisting of:

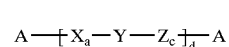

(i)

wherein:

each Y is independently variable and is selected from the group consisting of a single bond or

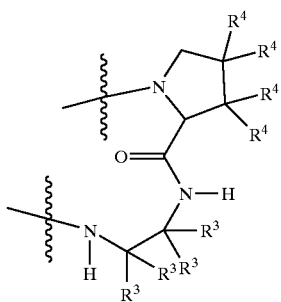

(ii)

wherein each $R^3$ in Formula (ii) is independently variable and is selected from the group consisting of hydrogen, linear or branched $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, and mono- or bicyclic heteroaryl-$C_1$–$C_6$-alkyl;

each $R^4$ in Formula (ii) is selected from the group of substituents as listed hereinbelow for $R^1$;

each X and each Z in Formula (i) is independently variable and is selected from the group consisting of γ-amino acid residues, provided that at least one of X or Z is a substituted or unsubstituted cyclically-constrained γ-amino acid residue independently selected from the group consisting of:

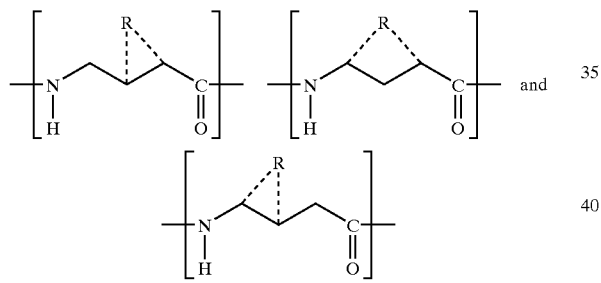

(iii)

and wherein R in Formula (iii), together with the carbons to which it is attached, independently defines a substituted or unsubstituted $C_5$ to $C_{10}$ cycloalkyl, cycloalkenyl, or heterocycle moiety, the heterocycle moiety having 1, 2, or 3 heteroatoms selected from the group consisting of N, S, and O;

and further wherein substituents on the cyclically-constrained γ-amino acid residue of Formula (iii) are independently selected from the group consisting of linear or branched $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, —$(CH_2)_{n+1}$—$OR^2$, —$(CH_2)_{n+1}$—$SR^2$, —$(CH_2)_{n+1}$—$S(=O)$—$CH_2$—$R^2$, —$(CH_2)_{n+1}$—$S(=O)_2$—$CH_2$—$R^2$, —$(CH_2)_{n+1}$—$NR^2R^2$, —$(CH_2)_{n+1}$—$NHC(=O)R^2$, —$(CH_2)_{n+1}$—$NHS(=O)_2$—$CH_2$—$R^2$, —$(CH_2)_{n+1}$—$O$—$(CH_2)_m$—$R^1$, —$(CH_2)_{n+1}$—$S$—$(CH_2)_m$—$R^1$, —$(CH_2)_{n+1}$—$S(=O)$—$(CH_2)_m$—$R^1$, —$(CH_2)_{n+1}$—$S(=O)_2$—$(CH_2)_m$—$R^1$, —$(CH_2)_{n+1}$—$NH$—$(CH_2)_m$—$R^1$, —$(CH_2)_{n+1}$—$N$—$\{(CH_2)_m$—$R^1\}_2$, —$(CH_2)_{n+1}$—$NHC(=O)$—$(CH_2)_{n+1}$—$R^1$, —$(CH_2)_{n+1}$—$NHS(=O)_2$—$(CH_2)_m$—$R^1$; —$(CH_2)_n$—$OR$, —$(CH_2)_n$—$SR^2$, —$(CH_2)_n$—$S(=O)$—$CH_2$—$R^2$, —$(CH_2)_n$—$S(=O)_2$—$CH_2$—$R^2$, —$(CH_2)_n$—$NR^2R^2$, —$(CH_2)_n$—$NHC(=O)R^2$, —$(CH_2)_n$—$NHS(=O)_2$—$CH_2$—$R^2$, —$(CH_2)_n$—$O$—$(CH_2)_m$—$R^1$, —$(CH_2)_n$—$S$—$(CH_2)_m$—$R^1$, —$(CH_2)_n$—$S(=O)$—$(CH_2)_m$—$R^1$, —$(CH_2)_n$—$S(=O)_2$—$(CH_2)_m$—$R^1$, —$(CH_2)_n$—$NH$—$(CH_2)_m$—$R^1$, —$(CH_2)_n$—$N$—$\{(CH_2)_m$—$R^1\}_2$, —$(CH_2)_n$—$NHC(=O)$—$(CH_2)_m$—$R^1$, and —$(CH_2)_n$—$NHS(=O)_2$—$(CH_2)_m$—$R^1$; wherein $R^2$ is independently selected from the group consisting of hydrogen, $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, and mono- or bicyclic heteroaryl-$C_1$–$C_6$-alkyl; and wherein $R^1$ is selected from the group consisting of hydroxy, $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; and mono- di- or tri-substituted urea, wherein the subsitutent(s) is selected from the group consisting of $C_1$–$C_6$-alkyl, aryl, heteroaryl; O-alkylurethane, O-arylurethane, and O-heteroarylurethane, and wherein m is an integer of from 2–6 and n is an integer of from 0–6;

wherein each "A" of Formula (i) is independently selected from the group consisting of hydrogen, hydroxy, an amino-terminus protecting group, and a carboxy-terminus protecting group;

wherein each of "a," "c," and "d" is an independently variable positive integer; and salts thereof.

2. The compound of claim 1, wherein a+c≧3.

3. The compound of claim 1, wherein Y is a single bond and a+c≧3.

4. The compound of claim 1, wherein Y is:

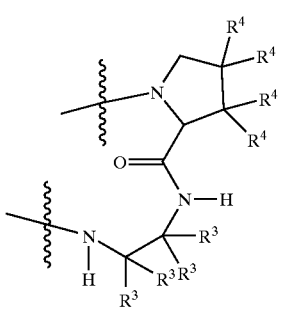

and a+c≧3.

5. The compound of claim 1, wherein Y is:

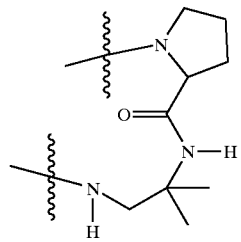

and a+c≧3.

6. The compound of claim 1, wherein each R, together with the carbons to which it is attached, independently defines a substituted or unsubstituted $C_5$ to $C_6$ cycloalkyl, cycloalkenyl, or heterocycle moiety having a single nitrogen heteroatom.

7. The compound of claim 1, wherein each R, together with the carbons to which it is attached, independently defines an unsubstituted $C_5$ to $C_6$ cycloalkyl, cycloalkenyl, or heterocycle moiety having a single nitrogen heteroatom.

8. The compound of claim 1, wherein R, together with the carbons to which it is attached, defines a substituted $C_5$ to $C_6$ cycloalkyl, cycloalkenyl, or heterocycle moiety having a single nitrogen heteroatom; and substituents on the cycloalkyl, cylcloalkenyl, or heterocycle moieties are independently selected from the group consisting of linear or branched $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, —$(CH_2)_{n+1}$—$OR^2$, —$(CH_2)_{n+1}$—$SR^2$, —$(CH_2)_{n+1}$—S(=O)—$CH_2$—$R^2$, —$(CH_2)_{n+1}$—S(=O)$_2$—$CH_2$—$R^2$, —$(CH_2)_{n+1}$—$NR^2R^2$, —$(CH_2)_{n+1}$—NHC(=O)$R^2$, —$(CH_2)_{n+1}$—NHS(=O)$_2$—$CH_2$—$R^2$, —$(CH_2)_{n+1}$—O—$(CH_2)_m$—$R^1$, —$(CH_2)_{n+1}$—S—$(CH_2)_m$—$R^1$, —$(CH_2)_{n+1}$—S(=O)—$(CH_2)_m$—$R^1$, —$(CH_2)_{n+1}$—S(=O)$_2$—$(CH_2)_m$—$R^1$, —$(CH_2)_{n+1}$—NH—$(CH_2)_m$—$R^1$, —$(CH_2)_{n+1}$—N—${(CH_2)_m$—$R^1}_2$, —$(CH_2)_{n+1}$—NHC(=O)—$(CH_2)_{n+1}$—$R^1$, —$(CH_2)_{n+1}$—NHS(=O)$_2$—$(CH_2)_m$—$R^1$, —$(CH_2)_n$—OR, —$(CH_2)_n$—$SR^2$, —$(CH_2)_n$—S(=O)—$CH_2$—$R^2$, —$(CH_2)_n$—S(=O)$_2$—$CH_2$—$R^2$, —$(CH_2)_n$—$NR^2R^2$, —$(CH_2)_n$—NHC(=O)$R^2$, —$(CH_2)_n$—NHS(=O)$_2$—$CH_2$—$R^2$, —$(CH_2)_n$—O—$(CH_2)_m$—$R^1$, —$(CH_2)_n$S—$(CH_2)_m$—$R^1$, —$(CH_2)_n$—S(=O)—$(CH_2)_m$—$R^1$, —$(CH_2)_n$—S(=O)$_2$—$(CH_2)_m$—$R^1$, —$(CH_2)_n$—NH—$(CH_2)_m$—$R^1$, —$(CH_2)_n$—N—${(CH_2)_m$—$R^1}_2$, —$(CH_2)_n$—NHC(=O)—$(CH_2)_m$—$R^1$, and —$(CH_2)_n$—NHS(=O)$_2$—$(CH_2)_m$—$R^1$;

wherein $R^2$ is independently selected from the group consisting of hydrogen, $C_1$–$C_6$-alkyl, alkenyl, or alkynyl; mono- or bicyclic aryl, mono- or bicyclic heteraryl having up to 5 heteroatoms selected from N, O, and S; mono- or bicyclic aryl-$C_1$–$C_6$-alkyl, mono- or bicyclic heteroaryl-$C_1$–$C_6$-alkyl; and wherein $R^1$ is selected from the group consisting of hydroxy, $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$–$C_6$-alkyl, aryl, heteroaryl; O-alkylurethane, O-arylurethane, and O-heteroarylurethane;

m is an integer of from 2–6 and n is an integer of from 0–6; and salts thereof.

9. The compound of claim 1, wherein each R, together with the carbons to which it is attached, independently defines a substituted or unsubstituted cyclopentyl, substituted or unsubstituted cyclohexyl, unsubstituted or N-substituted piperidinyl, or unsubstituted or N-substituted pyrrolidinyl.

10. The compound of claim 1, wherein at least one of X or Z is a cyclically-constrained γ-amino acid residue independently selected from the group consisting of:

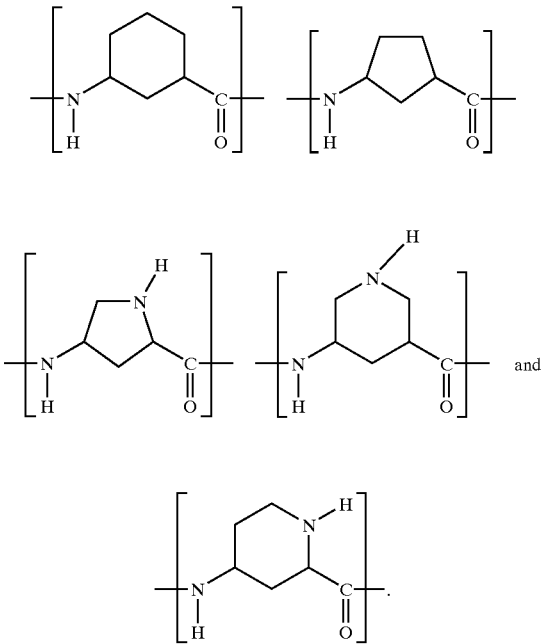

11. The compound of claim 1, wherein at least one of X or Z is a cyclically-constrained γ-amino acid residue independently selected from the group consisting of:

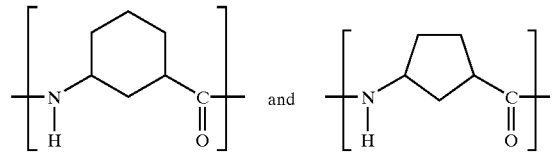

12. The compound of claim 1, wherein at least one of X or Z is a cyclically-constrained γ-amino acid residue selected from the group consisting of:

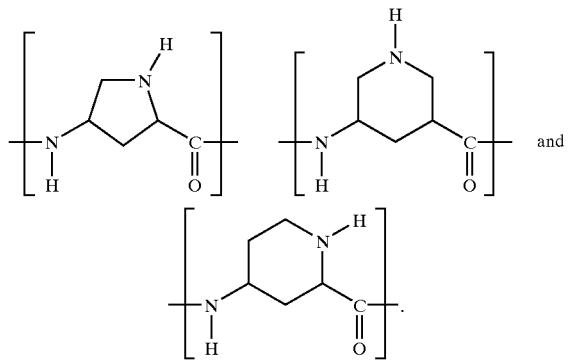

and

13. The compound of claim 1, wherein at least one of X or Z is a cyclically-constrained γ-amino acid residue selected from the group consisting of:

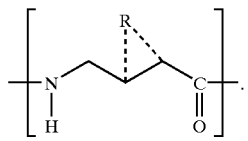

14. The compound of claim 13, wherein each R, together with the carbons to which it is attached, independently defines a substituted or unsubstituted $C_5$ to $C_6$ cycloalkyl, cycloalkenyl, or heterocycle moiety having a single nitrogen heteroatom.

15. The compound of claim 13, wherein each R, together with the carbons to which it is attached, independently defines an unsubstituted $C_5$ to $C_6$ cycloalkyl, cycloalkenyl, or heterocycle moiety having a single nitrogen heteroatom.

16. The compound of claim 13, wherein each R, together with the carbons to which it is attached, independently defines a substituted or unsubstituted cyclopentyl, substituted or unsubstituted cyclohexyl, unsubstituted or N-substituted piperidinyl, or unsubstituted or N-substituted pyrrolidinyl.

17. The compound of claim 1, wherein at least one of X or Z is a cyclically-constrained γ-amino acid residue independently selected from the group consisting of:

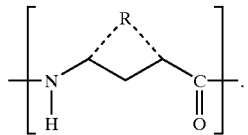

18. The compound of claim 17, wherein each R, together with the carbons to which it is attached, independently defines a substituted or unsubstituted $C_5$ to $C_6$ cycloalkyl, cycloalkenyl, or heterocycle moiety having a single nitrogen heteroatom.

19. The compound of claim 17, wherein each R, together with the carbons to which it is attached, independently defines an unsubstituted $C_5$ to $C_6$ cycloalkyl, cycloalkenyl, or heterocycle moiety having a single nitrogen heteroatom.

20. The compound of claim 17, wherein each R, together with the carbons to which it is attached, independently defines a substituted or unsubstituted cyclopentyl, substituted or unsubstituted cyclohexyl, unsubstituted or N-substituted piperidinyl, or unsubstituted or N-substituted pyrrolidinyl.

21. The compound of claim 1, wherein at least one of X or Z is a cyclically-constrained γ-amino acid residue independently selected from the group consisting of:

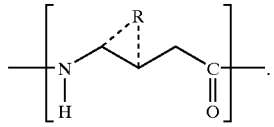

22. The compound of claim 21, wherein each R, together with the carbons to which it is attached, independently defines a substituted or unsubstituted $C_5$ to $C_6$ cycloalkyl, cycloalkenyl, or heterocycle moiety having a single nitrogen heteroatom.

23. The compound of claim 21, wherein each R, together with the carbons to which it is attached, independently defines an unsubstituted $C_5$ to $C_6$ cycloalkyl, cycloalkenyl, or heterocycle moiety having a single nitrogen heteroatom.

24. The compound of claim 21, wherein each R, together with the carbons to which it is attached, independently defines a substituted or unsubstituted cyclopentyl, substituted or unsubstituted cyclohexyl, unsubstituted or N-substituted piperidinyl, or unsubstituted or N-substituted pyrrolidinyl.

25. The compound of claim 1, wherein when Y is a single bond, one of the "A" moieties is a hydrogen or a amino-terminus protecting group, and the other of the "A" moieties is a hydroxy or a carboxy-terminus protecting group; and when Y is not a single bond, both of the "A" moieties are hydrogens or amino-terminus protecting groups.

26. A method of probing, disrupting, or mimicking binding interactions between two protein molecules or fragments thereof, the method comprising:
  in an in vivo, in vitro, or ex vivo reaction between the two proteins,
  (a) introducing to the reaction an unnatural polypeptide compound according to claim 1; and then
  (b) quantifying any effect of the added compound from step (a) on thermodynamic or kinetic parameters of the binding interaction between the two protein molecules or fragments thereof.

* * * * *